United States Patent
Kim

(10) Patent No.: US 10,851,355 B2
(45) Date of Patent: Dec. 1, 2020

(54) ISPETASE VARIANTS

(71) Applicant: KYUNGPOOK NATIONAL UNIVERSITY INDUSTRY-ACADEMIC COOPERATION FOUNDATION, Daegu (KR)

(72) Inventor: Kyung Jin Kim, Daegu (KR)

(73) Assignee: KYUNGPOOK NATIONAL UNIVERSITY INDUSTRY-ACADEMIC COOPERATION FOUNDATION

( * ) Notice: Subject to any disclaimer, the term of this patent is extended or adjusted under 35 U.S.C. 154(b) by 0 days.

(21) Appl. No.: 16/443,966

(22) Filed: Jun. 18, 2019

(65) Prior Publication Data
US 2020/0048621 A1 Feb. 13, 2020

(30) Foreign Application Priority Data

Aug. 8, 2018 (KR) .................. 10-2018-0092540
Feb. 14, 2019 (KR) .................. 10-2019-0017256

(51) Int. Cl.
*C12N 9/18* (2006.01)
*C12N 1/20* (2006.01)
*C12N 15/52* (2006.01)

(52) U.S. Cl.
CPC ............... *C12N 9/18* (2013.01); *C12N 1/20* (2013.01); *C12N 15/52* (2013.01)

(58) Field of Classification Search
None
See application file for complete search history.

(56) References Cited

FOREIGN PATENT DOCUMENTS

WO 2015025861 A1 2/2015

OTHER PUBLICATIONS

Bornscheuer et al. Curr Protoc Protein Sci. Nov. 2011;Chapter 26:Unit26.7. (Year: 2011).*
Li et al. Biotechnol Bioeng. Jul. 2014;111(7):1273-87. Epub May 6, 2014. (Year: 2014).*
Liu et al. Chembiochem. Jul. 16, 2018;19(14):1471-1475. Epub May 28, 2018. (Year: 2018).*
Accession A0A0K8P6T7. Nov. 11, 2015 (Year: 2015).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Seongjoon Joo et al. "Structural Insight Into Molecular Mechanism of Poly(Ethylene Terephthalate) Degradation" Nature Communications., 9:382 (2018).
Shosuke Yoshida et al. "A Bacterium That Degrades and Assimilates Poly(Ethylene Terephthalate)" Research Reports., vol. 351 ISSUE6278.
RCSB Protein data bank—5YNS.
Notice of Allowance from Korean Patent Office in Application No. KR 10-2019-0017256 dated Jan. 21, 2020. 5 pages.

* cited by examiner

*Primary Examiner* — Christian L Fronda
(74) *Attorney, Agent, or Firm* — Dilworth IP, LLC

(57) ABSTRACT

Disclosed are a method for preparing crystals of IsPETase protein, a method for screening an IsPETase protein activity regulator and IsPETase variants using a conformation of the protein crystal, a method for screening, IsPETase variants with increased PETase activity, and a method for decomposing PET using the variants. According to exemplary embodiments of the present invention, it is possible to determine a method for effectively preparing a crystal of the IsPETase protein and to obtain the resulting crystal thereof. Further, according to exemplary embodiments of the present invention, it is possible to identify a tertiary structure of the IsPETase from the crystal thereof and to prepare the variant with an increased PETase activity based on this structure. The IsPETase variant may be used effectively in the PET decomposition field.

7 Claims, 12 Drawing Sheets

Specification includes a Sequence Listing.

FIG. 3A
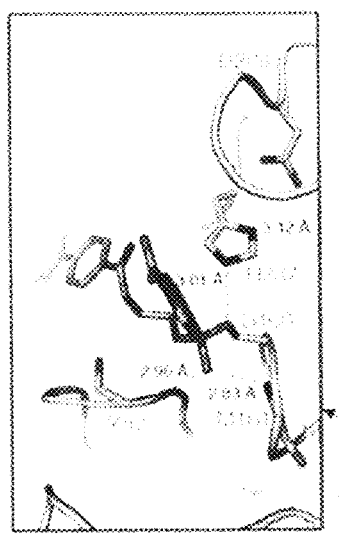
FIG. 3C
FIG. 3B
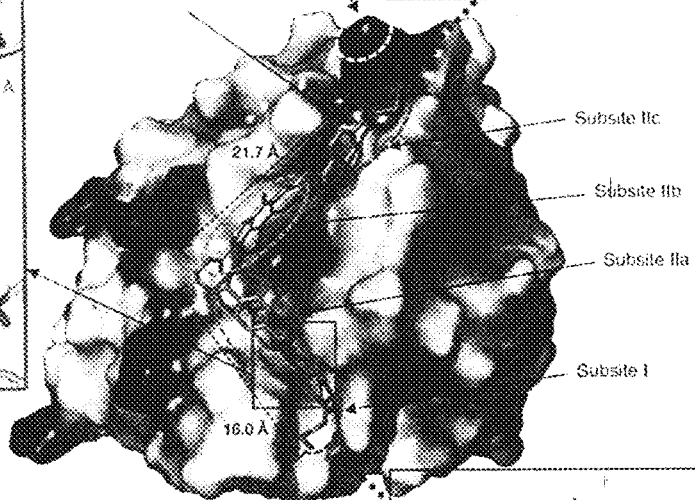
FIG. 3D
FIG. 3E
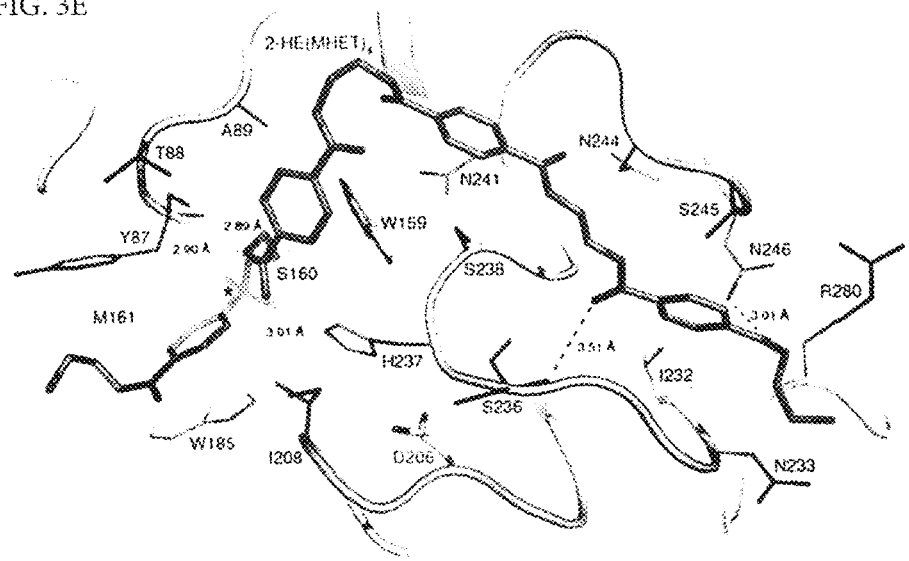

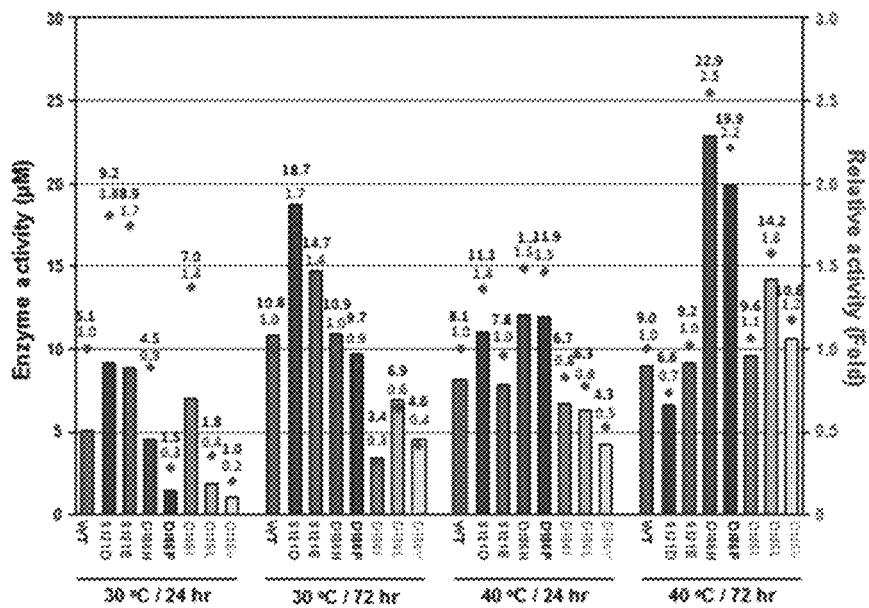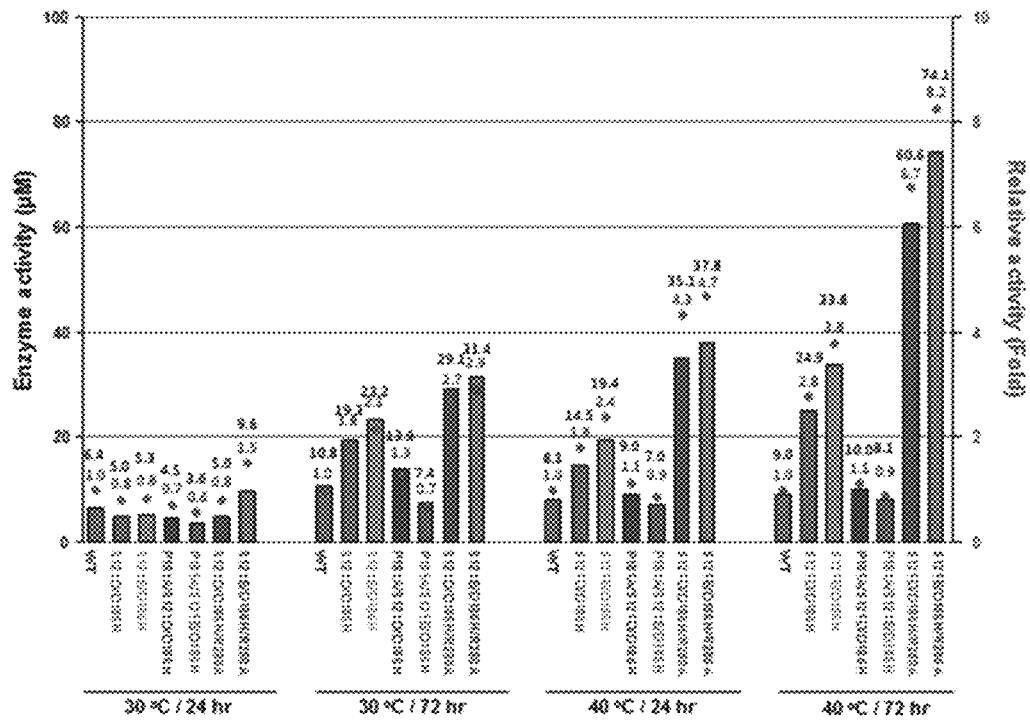

SEQUENCE LISTING

```
<160> NUMBER OF SEQ ID NOS: 4

<210> SEQ ID NO 1
<211> LENGTH: 290
<212> TYPE: PRT
<213> ORGANISM: Artificial Sequence
<220> FEATURE:
<223> OTHER INFORMATION: PETase of Ideonella sakaiensis

<400> SEQUENCE: 1

Met Asn Phe Pro Arg Ala Ser Arg Leu Met Gln Ala Ala Val Leu Gly
1               5                   10                  15

Gly Leu Met Ala Val Ser Ala Ala Ala Thr Ala Gln Thr Asn Pro Tyr
            20                  25                  30

Ala Arg Gly Pro Asn Pro Thr Ala Ala Ser Leu Glu Ala Ser Ala Gly
        35                  40                  45

Pro Phe Thr Val Arg Ser Phe Thr Val Ser Arg Pro Ser Gly Tyr Gly
    50                  55                  60

Ala Gly Thr Val Tyr Tyr Pro Thr Asn Ala Gly Gly Thr Val Gly Ala
65                  70                  75                  80

Ile Ala Ile Val Pro Gly Tyr Thr Ala Arg Gln Ser Ser Ile Lys Trp
                85                  90                  95

Trp Gly Pro Arg Leu Ala Ser His Gly Phe Val Val Ile Thr Ile Asp
            100                 105                 110

Thr Asn Ser Thr Leu Asp Gln Pro Ser Ser Arg Ser Ser Gln Gln Met
        115                 120                 125

Ala Ala Leu Arg Gln Val Ala Ser Leu Asn Gly Thr Ser Ser Ser Pro
    130                 135                 140

Ile Tyr Gly Lys Val Asp Thr Ala Arg Met Gly Val Met Gly Trp Ser
145                 150                 155                 160

Met Gly Gly Gly Gly Ser Leu Ile Ser Ala Ala Asn Asn Pro Ser Leu
                165                 170                 175

Lys Ala Ala Ala Pro Gln Ala Pro Trp Asp Ser Ser Thr Asn Phe Ser
            180                 185                 190

Ser Val Thr Val Pro Thr Leu Ile Phe Ala Cys Glu Asn Asp Ser Ile
        195                 200                 205

Ala Pro Val Asn Ser Ser Ala Leu Pro Ile Tyr Asp Ser Met Ser Arg
    210                 215                 220

Asn Ala Lys Gln Phe Leu Glu Ile Asn Gly Gly Ser His Ser Cys Ala
225                 230                 235                 240

Asn Ser Gly Asn Ser Asn Gln Ala Leu Ile Gly Lys Lys Gly Val Ala
                245                 250                 255

Trp Met Lys Arg Phe Met Asp Asn Asp Thr Arg Tyr Ser Thr Phe Ala
            260                 265                 270

Cys Glu Asn Pro Asn Ser Thr Arg Val Ser Asp Phe Arg Thr Ala Asn
        275                 280                 285

Cys Ser
290
```

```
<210> SEQ ID NO 2
<211> LENGTH: 290
<212> TYPE: PRT
<213> ORGANISM: Artificial Sequence
<220> FEATURE:
<223> OTHER INFORMATION: modified PETase of Ideonella
      sakaiensis_IsPETaseR280A

<400> SEQUENCE: 2
```

| Met | Asn | Phe | Pro | Arg | Ala | Ser | Arg | Leu | Met | Gln | Ala | Ala | Val | Leu | Gly |
|---|---|---|---|---|---|---|---|---|---|---|---|---|---|---|---|
| 1 | | | | 5 | | | | | 10 | | | | | 15 | |

| Gly | Leu | Met | Ala | Val | Ser | Ala | Ala | Thr | Ala | Gln | Thr | Asn | Pro | Tyr |
|---|---|---|---|---|---|---|---|---|---|---|---|---|---|---|
| | | | 20 | | | | | 25 | | | | | 30 | |

| Ala | Arg | Gly | Pro | Asn | Pro | Thr | Ala | Ala | Ser | Leu | Glu | Ala | Ser | Ala | Gly |
|---|---|---|---|---|---|---|---|---|---|---|---|---|---|---|---|
| | | | 35 | | | | | 40 | | | | | 45 | | |

| Pro | Phe | Thr | Val | Arg | Ser | Phe | Thr | Val | Ser | Arg | Pro | Ser | Gly | Tyr | Gly |
|---|---|---|---|---|---|---|---|---|---|---|---|---|---|---|---|
| | 50 | | | | | 55 | | | | | 60 | | | | |

| Ala | Gly | Thr | Val | Tyr | Tyr | Pro | Thr | Asn | Ala | Gly | Gly | Thr | Val | Gly | Ala |
|---|---|---|---|---|---|---|---|---|---|---|---|---|---|---|---|
| 65 | | | | | 70 | | | | | 75 | | | | | 80 |

| Ile | Ala | Ile | Val | Pro | Gly | Tyr | Thr | Ala | Arg | Gln | Ser | Ser | Ile | Lys | Trp |
|---|---|---|---|---|---|---|---|---|---|---|---|---|---|---|---|
| | | | | 85 | | | | | 90 | | | | | 95 | |

| Trp | Gly | Pro | Arg | Leu | Ala | Ser | His | Gly | Phe | Val | Val | Ile | Thr | Ile | Asp |
|---|---|---|---|---|---|---|---|---|---|---|---|---|---|---|---|
| | | | 100 | | | | | 105 | | | | | 110 | | |

| Thr | Asn | Ser | Thr | Leu | Asp | Gln | Pro | Ser | Ser | Arg | Ser | Ser | Gln | Gln | Met |
|---|---|---|---|---|---|---|---|---|---|---|---|---|---|---|---|
| | | 115 | | | | | 120 | | | | | 125 | | | |

| Ala | Ala | Leu | Arg | Gln | Val | Ala | Ser | Leu | Asn | Gly | Thr | Ser | Ser | Ser | Pro |
|---|---|---|---|---|---|---|---|---|---|---|---|---|---|---|---|
| | 130 | | | | | 135 | | | | | 140 | | | | |

| Ile | Tyr | Gly | Lys | Val | Asp | Thr | Ala | Arg | Met | Gly | Val | Met | Gly | Trp | Ser |
|---|---|---|---|---|---|---|---|---|---|---|---|---|---|---|---|
| 145 | | | | | 150 | | | | | 155 | | | | | 160 |

| Met | Gly | Gly | Gly | Gly | Ser | Leu | Ile | Ser | Ala | Ala | Asn | Asn | Pro | Ser | Leu |
|---|---|---|---|---|---|---|---|---|---|---|---|---|---|---|---|
| | | | | 165 | | | | | 170 | | | | | 175 | |

| Lys | Ala | Ala | Ala | Pro | Gln | Ala | Pro | Trp | Asp | Ser | Ser | Thr | Asn | Phe | Ser |
|---|---|---|---|---|---|---|---|---|---|---|---|---|---|---|---|
| | | | 180 | | | | | 185 | | | | | 190 | | |

| Ser | Val | Thr | Val | Pro | Thr | Leu | Ile | Phe | Ala | Cys | Glu | Asn | Asp | Ser | Ile |
|---|---|---|---|---|---|---|---|---|---|---|---|---|---|---|---|
| | | 195 | | | | | 200 | | | | | 205 | | | |

| Ala | Pro | Val | Asn | Ser | Ser | Ala | Leu | Pro | Ile | Tyr | Asp | Ser | Met | Ser | Arg |
|---|---|---|---|---|---|---|---|---|---|---|---|---|---|---|---|
| | 210 | | | | | 215 | | | | | 220 | | | | |

| Asn | Ala | Lys | Gln | Phe | Leu | Glu | Ile | Asn | Gly | Gly | Ser | His | Ser | Cys | Ala |
|---|---|---|---|---|---|---|---|---|---|---|---|---|---|---|---|
| 225 | | | | | 230 | | | | | 235 | | | | | 240 |

| Asn | Ser | Gly | Asn | Ser | Asn | Gln | Ala | Leu | Ile | Gly | Lys | Lys | Gly | Val | Ala |
|---|---|---|---|---|---|---|---|---|---|---|---|---|---|---|---|
| | | | | 245 | | | | | 250 | | | | | 255 | |

| Trp | Met | Lys | Arg | Phe | Met | Asp | Asn | Asp | Thr | Arg | Tyr | Ser | Thr | Phe | Ala |
|---|---|---|---|---|---|---|---|---|---|---|---|---|---|---|---|
| | | | 260 | | | | | 265 | | | | | 270 | | |

| Cys | Glu | Asn | Pro | Asn | Ser | Thr | Ala | Val | Ser | Asp | Phe | Arg | Thr | Ala | Asn |
|---|---|---|---|---|---|---|---|---|---|---|---|---|---|---|---|
| | | 275 | | | | | 280 | | | | | 285 | | | |

| Cys | Ser |
|---|---|
| | 290 |

```
<210> SEQ ID NO 3
<211> LENGTH: 290
<212> TYPE: PRT
<213> ORGANISM: Artificial Sequence
<220> FEATURE:
<223> OTHER INFORMATION: modified PETase of Ideonella
      sakaiensis_IsPETaseS121D/D186H/R280A

<400> SEQUENCE: 3
```

Met Asn Phe Pro Arg Ala Ser Arg Leu Met Gln Ala Ala Val Leu Gly
1               5                   10                  15

Gly Leu Met Ala Val Ser Ala Ala Thr Ala Gln Thr Asn Pro Tyr
            20                  25                  30

Ala Arg Gly Pro Asn Pro Thr Ala Ala Ser Leu Glu Ala Ser Ala Gly
            35                  40                  45

Pro Phe Thr Val Arg Ser Phe Thr Val Ser Arg Pro Ser Gly Tyr Gly
50                  55                  60

Ala Gly Thr Val Tyr Tyr Pro Thr Asn Ala Gly Gly Thr Val Gly Ala
65              70                  75                  80

Ile Ala Ile Val Pro Gly Tyr Thr Ala Arg Gln Ser Ser Ile Lys Trp
                85                  90                  95

Trp Gly Pro Arg Leu Ala Ser His Gly Phe Val Val Ile Thr Ile Asp
            100                 105                 110

Thr Asn Ser Thr Leu Asp Gln Pro Asp Ser Arg Ser Ser Gln Gln Met
            115                 120                 125

Ala Ala Leu Arg Gln Val Ala Ser Leu Asn Gly Thr Ser Ser Ser Pro
130                 135                 140

Ile Tyr Gly Lys Val Asp Thr Ala Arg Met Gly Val Met Gly Trp Ser
145                 150                 155                 160

Met Gly Gly Gly Gly Ser Leu Ile Ser Ala Ala Asn Asn Pro Ser Leu
                165                 170                 175

Lys Ala Ala Ala Pro Gln Ala Pro Trp His Ser Ser Thr Asn Phe Ser
            180                 185                 190

Ser Val Thr Val Pro Thr Leu Ile Phe Ala Cys Glu Asn Asp Ser Ile
            195                 200                 205

Ala Pro Val Asn Ser Ser Ala Leu Pro Ile Tyr Asp Ser Met Ser Arg
210                 215                 220

Asn Ala Lys Gln Phe Leu Glu Ile Asn Gly Gly Ser His Ser Cys Ala
225                 230                 235                 240

Asn Ser Gly Asn Ser Asn Gln Ala Leu Ile Gly Lys Lys Gly Val Ala
                245                 250                 255

Trp Met Lys Arg Phe Met Asp Asn Asp Thr Arg Tyr Ser Thr Phe Ala
            260                 265                 270

Cys Glu Asn Pro Asn Ser Thr Ala Val Ser Asp Phe Arg Thr Ala Asn
            275                 280                 285

Cys Ser
    290

<210> SEQ ID NO 4
<211> LENGTH: 290
<212> TYPE: PRT
<213> ORGANISM: Artificial Sequence
<220> FEATURE:
<223> OTHER INFORMATION: modified PETase of Ideonella
      sakaiensis_IsPETaseS121E/D186H/R280A

<400> SEQUENCE: 4

Met Asn Phe Pro Arg Ala Ser Arg Leu Met Gln Ala Ala Val Leu Gly
1               5                   10                  15

Gly Leu Met Ala Val Ser Ala Ala Thr Ala Gln Thr Asn Pro Tyr
            20                  25                  30

Ala Arg Gly Pro Asn Pro Thr Ala Ala Ser Leu Glu Ala Ser Ala Gly
            35                  40                  45

Pro Phe Thr Val Arg Ser Phe Thr Val Ser Arg Pro Ser Gly Tyr Gly

```
                    50                  55                  60
Ala Gly Thr Val Tyr Tyr Pro Thr Asn Ala Gly Gly Thr Val Gly Ala
 65                  70                  75                  80

Ile Ala Ile Val Pro Gly Tyr Thr Ala Arg Gln Ser Ser Ile Lys Trp
                 85                  90                  95

Trp Gly Pro Arg Leu Ala Ser His Gly Phe Val Val Ile Thr Ile Asp
            100                 105                 110

Thr Asn Ser Thr Leu Asp Gln Pro Glu Ser Arg Ser Ser Gln Gln Met
            115                 120                 125

Ala Ala Leu Arg Gln Val Ala Ser Leu Asn Gly Thr Ser Ser Ser Pro
            130                 135                 140

Ile Tyr Gly Lys Val Asp Thr Ala Arg Met Gly Val Met Gly Trp Ser
145                 150                 155                 160

Met Gly Gly Gly Gly Ser Leu Ile Ser Ala Ala Asn Asn Pro Ser Leu
                165                 170                 175

Lys Ala Ala Ala Pro Gln Ala Pro Trp His Ser Ser Thr Asn Phe Ser
            180                 185                 190

Ser Val Thr Val Pro Thr Leu Ile Phe Ala Cys Glu Asn Asp Ser Ile
            195                 200                 205

Ala Pro Val Asn Ser Ser Ala Leu Pro Ile Tyr Asp Ser Met Ser Arg
210                 215                 220

Asn Ala Lys Gln Phe Leu Glu Ile Asn Gly Gly Ser His Ser Cys Ala
225                 230                 235                 240

Asn Ser Gly Asn Ser Asn Gln Ala Leu Ile Gly Lys Lys Gly Val Ala
                245                 250                 255

Trp Met Lys Arg Phe Met Asp Asn Asp Thr Arg Tyr Ser Thr Phe Ala
            260                 265                 270

Cys Glu Asn Pro Asn Ser Thr Ala Val Ser Asp Phe Arg Thr Ala Asn
            275                 280                 285

Cys Ser
    290
```

ISPETASE VARIANTS

CROSS-REFERENCE TO RELATED APPLICATIONS

This application claims priority to and the benefit of Korean Patent Application No. 10-2018-0092540 filed in the Korean Intellectual Property Office on Aug. 8, 2018 and 10-2019-0017256 filed in the Korean Intellectual Property Office on Feb. 14, 2019, the entire contents of which are incorporated herein by reference.

TECHNICAL FIELD

The present invention relates to a method for preparing crystals of IsPETase protein, a method for screening an IsPETase protein activity regulator using a conformation of the protein crystal, a method for screening IsPETase variants, IsPETase variants with increased PETase activity, and a method for decomposing PET using the variants.

BACKGROUND ART

Plastics are essential materials in life because of their desirable properties such as lightness, durability, low cost, easy formability in various forms and non-degradability. However, due to the non-degradability considered to be a major advantage in using plastics, waste plastics have been accumulated in landfills and oceans and are considered as a major cause of environmental problems. The production of plastics is steadily increasing, thereby producing around 320 million tons worldwide in 2015. Since most plastics are robust against being biodegradable and it takes a long time for the plastics to decompose, an accumulated amount of plastic wastes is expected to reach 33 billion tons by 2050. Thus, much effort is being made to reduce plastic wastes. Various chemical decomposition methods such as glycolysis, methanolysis, hydrolysis, aminolysis and ammonolysis have been developed to remove plastic wastes and recycle plastic-based materials. However, these methods generally require high temperature conditions and often produce additional environmental pollutants. Therefore, when biocatalytic decomposition is applied in an environmentally friendly manner, this may be an alternative method. Microorganisms may be colonized on the material surface and decompose the plastic materials through enzymatic hydrolysis of ester bonds. The biodegradability of plastics depends on their chemical and physical properties.

Poly(ethylene terephthalate) (PET) is a widely used polyester and is resistant to biodegradation. According to a report by the US National Park Service, it takes about 450 years to decompose a PET bottle. PET is polymerized via the ester bond between terephthalate (TPA) and ethylene glycol (EG). Various bacterial hydrolases, such as cutinase, lipase, carboxylesterase, and esterase emerge to decompose PET, although decomposition degrees thereof are different. Among the PET-degrading enzymes identified so far, *Thermobifida fusca* DSM43793-derived TfH and TfH BTA-2, *Thermobifida fusca* KW3-derived TfCut1 and TfCut2, plant compost metagenome-derived LC cutinase, *Saccharomonospora viridis* AHK190-derived cutinase, *Thermomyces insolens*-derived HiC, and *Candida Antarctica*-derived lipase B emerge to have a relatively high decomposition ability. However, the decomposition activity thereof for industrial applications is still too low.

Several strategies have been adopted to increase the enzymatic activity. Using site-directed mutagenesis of the active site, the cutinase exhibits higher hydrolysis activity. Further, introduction of $Ca^{2+}$ or $Mg^{2+}$ ions into esterase or addition of disulfide bonds to esterase improves the thermal stability of the enzyme, which leads to improvement of PET decomposition property. Recently, dual enzyme system consisting of *T. fusca* KW3-derived TfCut2 and LC cutinase; or a dual enzyme system consisting of *C. antarctica*-derived lipase and *Humicola insolens*-derived cutinase has been found to exhibit a synergistic effect. However, despite these attempts, the PET decomposition activities thereof are still low.

Recently, *Ideonella sakaiensis* has been isolated as a new bacterial species that can use PET as a carbon source. *I. sakaiensis* PETase (IsPETase) can decompose PET at a suitable temperature (30° C.) and has a relatively higher PET decomposition activity compared to other PET decomposition enzymes such as cutinase and lipase (Yoshida, S. et al. Science 351, 1196-1199, 2016). Further, because the IsPETase exhibits a higher specificity to PET, the excellent ability of IsPETase to perform the PET decomposition has attracted much attention. However, detailed enzyme mechanism thereof is not clarified, and further research thereof is difficult.

Based on this background, the present inventors have tried to reveal a crystal structure and structural characteristics of IsPETase. Thus, we have identified a method for the efficient production of protein crystals of IsPETase, and the crystals were obtained. Further, we have identified a tertiary structure of IsPETase from the crystal. Based on this structure, we have confirmed variants thereof with increased PETase activity. In this manner, we have completed the present invention.

SUMMARY OF THE INVENTION

The present invention has been made in an effort to provide an IsPETase variant having one or more amino acid substitutions in an amino acid sequence represented by SEQ ID NO: 1 in which the IsPETase variant includes the amino acid substitution of R280A.

Another purpose of the present invention is to provide polynucleotides encoding the IsPETase variant.

Another purpose of the present invention is to provide a recombinant vector including a polynucleotide encoding the IsPETase variant.

Another purpose of the present invention is to provide microorganisms transformed to include the IsPETase variant and the protein.

Another purpose of the present invention is to provide a method for decomposing poly(ethylene terephthalate) (PET) involving treating the IsPETase variant.

Another purpose of the present invention is to provide a method for preparing crystals of IsPETase protein, the method including mixing i) a reservoir solution containing polyethylene glycol (PEG) 10000, bis-tris and ammonium acetate, and ii) a protein solution containing IsPETase protein to form a mixed solution; and crystallizing the IsPETase protein via a vapor diffusion method of the mixed solution to form an IsPETase protein crystal.

Another purpose of the present invention is to provide a method for screening an IsPETase protein activity regulator, the method including (a) preparing or selecting IsPETase protein activity-regulating candidate peptides or IsPETase protein-binding candidate compounds using a conformation of the IsPETase protein; and (b) determining whether the candidate peptides or compounds selected or prepared in the step (a) regulate the activity of the IsPETase protein.

Another purpose of the present invention is to provide a method for screening IsPETase variants, the method including determining a substrate-binding site from a conformation of an IsPETase protein.

An exemplary embodiment of the present invention provides an IsPETase variant having one or more amino acid substitutions in an amino acid sequence represented by SEQ ID NO: 1 in which the IsPETase variant includes the amino acid substitution of R280A.

As used herein, a term "IsPETase" is a type of esterase that hydrolyzes ester-bonds using *Ideonella sakaiensis*-derived PET-degrading enzyme among PETases as an enzyme that decomposes the PET. The IsPETase decomposes the PET into monomers such as bis(2-hydroxyethyl) terephthalate (BHET), mono(2-hydroxyethyl) terephthalate (MHET), and terephthalic acid (TPA) (See FIG. 3A-3D).

As used herein, a term "IsPETase variant" includes peptides with one or more differences in an amino acid sequence compared to the IsPETase wild-type; that is, peptides resulting from modification of the IsPETase wild-type sequence.

Specifically, the IsPETase variant may be prepared by changing one or more amino acids in the IsPETase wild-type via at least one of a substitution, addition, deletion, modification, and combinations thereof.

As used herein, the IsPETase variant may have increased activity and thermal stability over the IsPETase wild-type. Specifically, the activity may be an activity measured based on BHET as a substrate or an activity measured based on a PET film as a substrate. However, the present invention is not limited thereto. The thermal stability may be measured by measuring a melting temperature (Tm) of IsPETase or may be measured based on the PET film as a substrate at high temperature (over 40° C.). The present invention is not limited thereto.

Specifically, the IsPETase variant may be, but is not limited to, an IsPETase variant that includes the amino acid substitution of R280A in the amino acid sequence represented by SEQ ID NO: 1. More specifically, the IsPETase variant may be an IsPETase variant that additionally includes one or more amino acid substitutions selected from the group consisting of amino acid substitutions of S121D and D186H in addition to the amino acid substitution of R280A. Alternatively, the IsPETase variant may be an IsPETase variant that additionally includes at least one amino acid substitution selected from the group consisting of amino acid substitutions of S121E and D186H in addition to the amino acid substitution of R280A. The present invention is not limited thereto.

In some embodiments, the IsPETase variant may further includes a amino acid substitution at position 121-th from N-terminal of SEQ ID NO: 1 with aspartic acid or a amino acid substitution at position 186-th from N-terminal of SEQ ID NO: 1, wherein the substitution of the 186th amino acid is replaced by any one of histidine, phenylalanine, isoleucine, leucine, and valine.

In some embodiments, the IsPETase variant may further incldues a amino acid substitution at position 121-th from N-terminal of SEQ ID NO: 1 with aspartic acid and a amino acid substitution at position 186-th from N-terminal of SEQ ID NO: 1, Wherein the substitution of the 186th amino acid is replaced by any one of histidine, phenylalanine, isoleucine, leucine, and valine.

In some embodiments, the IsPETase variant may further incldues a amino acid substitution at position 121-th from N-terminal of SEQ ID NO: 1 with glutamic acid or a amino acid substitution at position 186-th from N-terminal of SEQ ID NO: 1, Wherein the substitution of the 186th amino acid is replaced by any one of histidine, phenylalanine, isoleucine, leucine, and valine.

In some embodiments, the IsPETase variant may further incldues a amino acid substitution at position 121-th from N-terminal of SEQ ID NO: 1 with glutamic acid and a amino acid substitution at position 186-th from N-terminal of SEQ ID NO: 1, Wherein the substitution of the 186th amino acid is replaced by any one of histidine, phenylalanine, isoleucine, leucine, and valine.

More specifically, the IsPETase variant may be composed of an amino acid sequence represented by any one of SEQ ID NOS: 2 to 4. As used herein, the IsPETase variant may include a polypeptide having at least 80%, 90%, 95%, 96%, 97%, 98%, or 99% or more homology with residues 34 to 290 of the amino acid sequence represented by any one of SEQ ID NOS: 2 to 4. The present invention is not limited thereto. Further, when the amino acid sequence has this homology and exhibits an effect comparable to the above protein, it is obvious that supplementary proteins of the amino acid sequence with deletion, modification, substitution or addition of some amino acid sequences are also included within the scope of the present application.

The term "homology" refers to a degree of similarity of two given protein sequences, a degree to which they match a given amino acid sequence or base sequence. This degree may be expressed as a percentage. As used herein, a homologous sequence of the variant having the same or similar activity as a given amino acid sequence or base sequence may be indicated as "% homology". The sequences homology between one moiety to another may be determined by known techniques to the art. For example, a standard software (for example, BLAST 2.0) that computes parameters such as score, identity and similarity may be used to determine the homology. Alternatively, sequences may be compared using Southern hybridization experiments under defined stringent conditions to determine the homology. A suitable hybridization condition as defined may be within a range in the art and may be determined by a method well known to those skilled in the art (e.g., J. Sambrook et al., Molecular Cloning, A Laboratory Manual, $2^{nd}$ Edition, Cold Spring Harbor Laboratory press, Cold Spring Harbor, N.Y., 1989; F. M. Ausubel et al., Current Protocols in Molecular Biology, John Wiley & Sons, Inc., New York).

Another exemplary embodiment provides IsPETase variants including at least one amino acid substitution selected from a group consisting of amino acid substitutions of S160A, D206A, H237A, Y87A, M161A, W185A, I208A, W159A, S238A, N241A, S121D, S121E, D186H, D186F, D186I, D186L, D186V and R280A. More specifically, the IsPETase variant including the amino acid substitution of R280A, the IsPETase variant including amino acid substitutions of S121D and D186H, the IsPETase variant including amino acid substitutions of S121E and D186H, the IsPETase variant including amino acid substitutions of R280A, S121D and D186H, and the IsPETase variant including amino acid substitutions of R280A, S121E and D186H were prepared (Examples and 5). The present invention is not limited thereto. Further, the results of measuring the activity of the variants are as follows: the PETase activities of the IsPETase variant including the amino acid substitution of R280A, the IsPETase variant including amino acid substitutions of S121D and D186H, the IsPETase variant including amino acid substitutions of S121E and D186H, the IsPETase variant including amino acid substitutions of R280A, S121D and D186H, and the IsPETase variant including amino acid substitutions of R280A, S121E and D186H may be increased relative to the PETase activity of the IsPETase wild-type and lasts for a long time at a high temperature (40° C.) (FIGS. 5A-5C, 6, 10A-10B and 12A-12B).

Yet another exemplary embodiment provides a polynucleotide encoding the IsPETase variant, or a vector containing the polynucleotide.

The description of the "IsPETase" and the "IsPETase variant" is as described above.

As used herein, a term "polynucleotide" is a polymer of nucleotides in which nucleotide monomers are linked to each other in a long chain by a covalent bond and is a DNA or RNA strand longer than a certain length. More specifically, the polynucleotide refers to a polynucleotide fragment encoding the variant polypeptide.

A base sequence encoding the same amino acid sequence and variants thereof due to genetic code degeneracy may be included within the scope of the present application. A polynucleotide encoding the same amino acid sequence and variants thereof due to genetic code degeneracy may be included within the scope of the present application.

The polynucleotide sequence according to the present invention may be easily modified via substitution, deletion, insertion or combination of one or more bases. Thus, polynucleotides having at least 80%, 90%, 95%, 96%, 97%, 98%, or 99% or more homology with the base sequence represented by SEQ ID NO: 2, 3 or 4 should be interpreted as being included in the scope of the present application.

As used herein, a term "vector" refers to a DNA product containing a base sequence of a polynucleotide encoding the target protein operatively linked to a suitable regulation sequence so that the target protein can be expressed in the appropriate host. The regulation sequence may include a promoter that may initiate transcription, any operator sequence to regulate such transcription, a sequence that encodes a suitable mRNA ribosome-binding site, and a sequence that regulates the termination of transcription and translation. The vector may be transformed into a suitable host cell and then be replicated or functioned regardless of the host genome. The vector may be integrated within the host genome itself.

The vector used herein is not particularly limited as long as it is replicable in the host cell. Any vector known in the art may be used. Examples of commonly used vectors may include plasmids, cosmids, viruses and bacteriophages in their natural or recombinant state. For example, the phage vector or cosmid vector may include pWE15, M13, MBL3, MBL4, IXII, ASHII, APII, t10, t11, Charon4A, and Charon21A. The plasmid vector may include a pBR based vector or the like. Specifically, pDZ, pACYC177, pACYC184, pCL, pECCG117, pUC19, pBR322, pMW118, pCC1BAC vectors and the like may be used.

The term "operatively-linked" means that the gene sequence is functionally linked to a promoter sequence that initiates and mediates transcription of a polynucleotide encoding the target protein of the present invention. The operatively linkage may be made using known gene recombinant techniques in the art. A site-specific DNA cleavage and ligation may be performed using restriction enzyme and ligation enzymes in the art. The present invention is not limited thereto.

In one example, a polynucleotide encoding a target protein in a chromosome may be replaced with a modified polynucleotide via a vector for insertion chromosome into a cell. The insertion of the polynucleotide into the chromosome may be made by any method known in the art, for example, homologous recombination. The present invention is not limited thereto.

Still another exemplary embodiment provides a microorganism transformed with a recombinant vector containing a polynucleotide encoding the IsPETase variant. Specifically, introduction may be accomplished by transformation, but the present invention is not limited thereto.

In this connection, the description of the "IsPETase", "IsPETase variant", "polynucleotide" and "vector" is as described above.

As used herein, a term "transformation" refers to introducing a vector containing a polynucleotide encoding a target protein into a host cell so that the protein encoded by the polynucleotide can be expressed in the host cell. As long as the transformed polynucleotides can be expressed in the host cells, the transformed polynucleotides may be included in the chromosome of the host cell or may be located outside the chromosome. Further, as long as the polynucleotide may be introduced into the host cells and expressed, the polynucleotide may have any form. For example, the polynucleotide may be introduced into a host cell in the form of an expression cassette as a gene structure that contains all the elements needed for self-expression thereof. The expression cassette may include a promoter, a transcription termination signal, a ribosome-binding site, and a translation termination signal operatively linked to the polynucleotide. The expression cassette may be in a form of a self-replicating expression vector. Further, the polynucleotide may be introduced into the host cell in its own form and may be operatively linked to the sequence required for the expression thereof in the host cell. The present invention is not limited thereto.

The host cell used in transformation according to the present invention may be a host cell well known in the art. Specifically, the host cell may include a bacterial, fungal, yeast, plant or animal (e.g., mammal or insect) cell. More specifically, the host cell may be selected from the group consisting of *Escherichia coli*(*E. coli*) or *Corynebacterium glutamicum* strain. The present invention is not limited thereto.

Still yet another exemplary embodiment provides a method for decomposing poly(ethylene terephthalate) (PET) involving treating the IsPETase variant.

In this connection, the description of the "IsPETase" and the "IsPETase variant" is as described above.

In the method for decomposing PET, a composition including the IsPETase variant may be used. Alternatively, a device including the composition may be used. The present invention is not limited thereto. As long as the method for decomposing PET using the IsPETase variant is feasible, any approach may be included within the scope of the present application.

Still yet another exemplary embodiment provides a method for preparing crystals of IsPETase protein, the method including mixing i) a reservoir solution containing polyethylene glycol (PEG) 10000, bis-tris and ammonium acetate, and ii) a protein solution containing IsPETase protein to form a mixed solution; and crystallizing the IsPETase protein via a vapor diffusion method of the mixed solution to form an IsPETase protein crystal.

In this connection, the description of the "IsPETase" is as described above.

There are many different methods for analyzing a protein's crystal structure, and two main methods are NMR spectroscopy and X-ray crystallography. NMR Spectroscopy is based on the principle of predicting a distance between particular atoms in a molecule by analyzing signal changes due to chemical factor which can be detected in the NMR spectrum of a molecule. Data of the chemical shift obtained by the NMR test is analyzed to obtain a set of the distances between labeled atoms in one protein, and a model or a set of models satisfying information about all distances determined by the experiment is produced. Thus, there is a disadvantage of requiring collection and analysis of a large amount of data. Meanwhile, X-ray crystallography is based on the principle of obtaining the result by analyzing x-ray scattered by electron cloud surrounding an atom of the crystal in an x-ray generator. X-ray diffraction patterns from protein crystals are regular because the individual protein molecules are arranged in a regular lattice. Based on this principle, X-ray crystallography is a method of analyzing a protein structure by producing an electron density map of the protein using x-ray scattered and reflected from the protein crystals. However, there is a disadvantage of requiring protein crystallization, because of requiring pure protein samples. According to the present invention, the present inventors have identified a method capable of optimally producing IsPETase protein crystals. We obtained IsPETase protein crystals and performed X-ray analysis thereof to identify the conformation of the IsPETase protein.

As used herein, the phrase "allowing crystallization" or "having crystallinity" means that, in order to prepare a protein in a form suitable for X-ray analysis of its conformation, mutations are introduced into the protein molecule so as to form solid particles having a uniform shape and size from a uniform liquid or to further stabilize the crystal of the protein. The conformation of a protein is very important for the understanding of in vivo actions of the protein. That is, since an understanding of the arrangement and three-dimensional structure of atoms constituting a protein as a polymer makes it possible to analyze the conformation of the IsPETase protein and thus to produce the IsPETase variants with high PETase activity, it is important to identify the conformation of the protein.

The IsPETase protein crystal of the present invention has an amino acid sequence as shown in SEQ ID NO: 1. Specifically, the IsPETase protein crystal belongs to a space group $P2_12_12_1$ and has unit cell parameters a=43.48 Å, b=50.40 Å, and c=129.49 Å. The present invention is not limited thereto.

As used herein, the term "space group" refers to a symmetry of a unit cell of a crystal, and a combination of symmetry elements forms a group.

As used herein, the term "unit cell parameter" is also called a lattice constant. The unit cell is the smallest repeatable unit which constitutes the space group and is interpreted in the easiest manner. The unit cell may be defined using microcrystalline axes. The unit cell parameters may be lengths (a, b, c) for these three axes.

The crystallization of the IsPETase protein may be carried out by a variety of known crystallization methods, preferably, by a vapor diffusion method. The present invention is not limited thereto.

The vapor diffusion method may be a sitting drop vapor diffusion method or a hanging-drop vapor diffusion method, and more preferably, the hanging-drop vapor diffusion method, but is not limited thereto.

In the vapor diffusion method, the protein solution is equilibrated with a large aqueous reservoir solution containing a precipitant at a suitable concentration to prepare the crystal of the protein. Usually, a purified protein solution is mixed with an equal amount of a reservoir solution to bring the concentration of the precipitant to about a half thereof that is required for the crystallization. Then, the mixture solution is hung under a cover slip sealing a top of the reservoir or is attached to a top of the container. Then, the sealed container is left for 1 day to 1 year, usually for 2 to 6 weeks, so that the crystal of the protein grows larger. In the vapor diffusion method, when a micro-drop of mother liquor and a much larger reservoir solution exist separately in a closed space, transport of either water or other volatile agents occurs between them, leading to a supersaturated state in the solution condition of protein, and in such a thermodynamically metastable state, proteins are precipitated depending on the change of the precipitant. While the protein precipitation slowly occurs, stable crystals are formed and the precipitant functions to lower the solubility of the concentrated protein solution, and proteins congregate to form crystals in order to reduce an adsorption layer around protein molecules.

The reservoir solution contains a mixture of the precipitant, buffer, salt, and surfactant at different concentrations. Droplets are usually formed by mixing the protein solution with the reservoir solution of various conditions at a ratio of 1:1, and the droplets thus formed are placed on a microbridge, and sealed. At this time, there is a difference in the concentration between the proteins in the droplets and the reservoir solution in the initial stage, and thus the proteins do not exist as crystals. They are equilibrated while sealed, and crystals are formed under the specific conditions by the above described principle. As used herein, the term "hanging-drop vapor diffusion method" is a protein crystallization method, which provides crystals having a size sufficient for protein structural analysis. In the hanging-drop vapor diffusion method, a reagent containing a sample and a pure liquid reagent are placed on the top of the reservoir under vapor equilibration. To achieve equilibrium of the sample having a lower reagent contents than the reservoir, water contained in the sample eventually ends up in the reservoir. Water contained in the sample is removed until the concentration is approximately the same as that in the liquid reagent, and finally, protein crystals reaching the equilibration can be obtained.

In the vapor diffusion method, the type and proper concentration of the salt, the buffer and the surfactant as well as the precipitant in the reservoir solution, pH of the solution, and the experimental temperature vary depending on the type of protein, and in some cases, they become very important factors in crystal formation of proteins.

Thus, the present invention provides a method for preparing crystals of IsPETase protein optimized for crystal formation of the IsPETase protein.

The method for preparing crystals of IsPETase protein may include crystallizing of the IsPETase protein using a reservoir solution containing polyethylene glycol (PEG) 10000, bis-tris and ammonium acetate via a vapor diffusion method.

The polyethylene glycol 10000 may be contained in a reservoir solution as a precipitant and may have an unmodified or modified form. The present invention is not limited thereto. Specifically, the polyethylene glycol 10000 may be contained at a concentration of 10 to 20% (v/v), more specifically, at a concentration of 17%, but the present invention is not limited thereto.

The bis-tris may be contained in a reservoir solution as a buffer and may have an unmodified or modified form. The present invention is not limited thereto. Specifically, the bis-tris may be contained at a concentration of 0.01 to 1 M, more specifically at a concentration of 0.1 M. The present invention is not limited thereto. Further, the pH of the buffer may be 4.0 to 6.0, more specifically 5.0. The present invention is not limited thereto.

The ammonium acetate may be contained in a reservoir solution as a salt and may have an unmodified form or a modified form. The present invention is not limited thereto. Specifically, the ammonium acetate may be contained at a concentration of 0.01 to 1 M, more specifically at a concentration of 0.1 M, but the present invention is not limited thereto.

The protein solution containing the IsPETase protein may be added and mixed to the reservoir solution having the same composition as defined above. Then, the mixture solution may be equilibrated to prepare the crystal of the IsPETase protein.

In this connection, the protein solution containing the IsPETase protein may contain purified IsPETase protein. Specifically, the purified IsPETase protein may be contained in the protein solution at a concentration of 20 to 40 mg/ml, more specifically at a concentration of 28 mg/ml. The present invention is not limited thereto.

One embodiment of the present invention may include purifying the IsPETase protein, mixing the protein solution containing the purified IsPETase protein at a concentration of 28 mg/ml with 17% (v/v) polyethylene glycol 10000, 0.1 M bis-tris having pH 5.0 and 0.1 M ammonium acetate, and then performing the hanging-drop vapor diffusion method, thereby to prepare the crystal of the IsPETase protein (See Example 2-1).

Still yet another exemplary embodiment provides a method for screening an IsPETase protein activity regulator, the method including (a) producing or screening IsPETase protein activity-regulating candidate peptides or IsPETase protein-binding candidate compounds using a conformation of the IsPETase protein; and (b) determining whether the candidate peptides or compounds selected or prepared in the step (a) regulate the activity of the IsPETase protein.

In this connection, the description of the "IsPETase" is as described above.

Information on various protein sites including substrate-binding sites may be determined based on the conformation of the IsPETase protein as identified in accordance with the present invention.

The step (a) of the screening method may include identifying the conformation of the IsPETase protein, and production or screening of the IsPETase protein activity-regulating candidate peptides or the IsPETase protein-binding candidate compounds using the conformation.

In one embodiment of the present invention, the IsPETase protein crystals are obtained, and, after the X-ray analysis of the crystals, the structure and substrate-binding site of the IsPETase protein were identified.

Specifically, in one embodiment of the present invention, it was confirmed that the IsPETase crystal structure belongs to the α/β hydrolase superfamily, that a central twisted β-sheet is composed of nine mixed β-strands (β1 to β9) and is surrounded by seven α-helix strands (α1 to α7), and that the IsPETase contains conserved serine hydrolase Gly-x1-Ser-x2-Gly motif (Gly158-Trp159-Ser160-Met161-Gly162) located in the active site (See Example 2-3, and FIGS. 1A & 1B). Further, it was confirmed that the IsPETase does not form a hydrogen-bond between Pro181 residues in in a 6-th strand (β6-sheet) in the β-sheet and adjacent amino acids and does not form a hydrogen-bond between Asp186 residues and adjacent α-helix Ser121 residues (See Example 5-1, FIG. 7A-7C and FIG. 8A-8D).

It was confirmed that the substrate-binding site forms a long and shallow L-shaped gap on a flat surface with a value of about 25 Å and 29 Å, and that the substrate-binding site is composed of two subsites (See Example 2-4, and FIG. 3A-3D).

Therefore, we may prepare or select substances or binding-substances that regulate the activity of the IsPETase protein based on the active site and structural information, or sequence information, etc. of the IsPETase protein as defined above.

The step (b) of the screening method includes a step of determining whether the IsPETase protein regulation candidate peptide or compound as prepared or selected in the step (a) regulates the activity of the IsPETase protein. When the candidate substance inhibits the activity of the IsPETase protein, the substance may be considered as an IsPETase protein inhibitor. When the candidate substance increases the activity of the IsPETase protein, this substance may be considered as an IsPETase protein activity enhancer.

Still yet another exemplary embodiment provides a method for screening an IsPETase variant, the method including determining a substrate-binding site from the conformation of the IsPETase protein.

In this connection, the description of the "IsPETase" and "IsPETase variant" is as described above.

According to exemplary embodiments of the present invention, it is possible to determine a method for effectively producing the crystal of the IsPETase protein and to obtain the resulting crystal thereof. Further, according to exemplary embodiments of the present invention, it is possible to identify the tertiary structure of the IsPETase from the crystal thereof and to prepare the variant with an increased PETase activity based on this structure. The IsPETase variant may be used effectively in the PET decomposition field.

BRIEF DESCRIPTION OF THE DRAWINGS

FIG. 3A shows the docking model of the reaction intermediate of 2-HE(MHET)$_4$ and the catalyst triplet in the IsPETase. Three residues of Ser160, Asp206 and His237 forming the catalyst triplet are represented by sticks. The distance of interaction between the oxygen anion hole and the catalyst triplet is also shown. FIG. 3B shows the substrate-binding site of the IsPETase. The IsPETase structure is represented using an electrostatic potential surface model. The 2-HE(MHET)$_4$ docking model is represented by an stick. The cleavage site is highlighted with a box. The sub-sites I, IIa, IIb, and IIc of the substrate-binding site are represented by dotted circles. Arg280 residue located at the end of the sub-site IIc is shown. FIG. 3C shows a side view of the substrate binding mode of the IsPETase in FIG. 3B. FIG. 3D shows a side view of the substrate binding mode of the IsPETase in FIG. 3B. FIG. 3E shows the residue associated with the IsPETase active site. The IsPETase is represented by a cartoon diagram. The residue associated with the bond of 2-HE(MHET)$_4$ is represented by the line model. The ester-bonds that are cleaved by the enzyme are indicated by star marks. The 2-HE(MHET)$_4$ docking model is represented by an stick. The hydrogen-bond between the residue and the substrate is indicated by a line.

FIG. 10A shows the hydrolytic activity of IsPETase when using the PET film as a substrate. The PETase activity of the IsPETase is measured at an enzyme concentration of 200 nM. The amount of MHET as produced is monitored by HPLC analysis. FIG. 10B shows the hydrolytic activity of the IsPETase variant when using the PET film as a substrate. The PETase activity of the IsPETase variant is measured at an enzyme concentration of 200 nM. The amount of MHET as produced is monitored by HPLC analysis. PETase activities at 24 and 72 hours of the IsPETase variant are compared with those of the IsPETase$^{W/T}$ at 30° C. and 40° C.

DETAILED DESCRIPTION

Figure 1A:
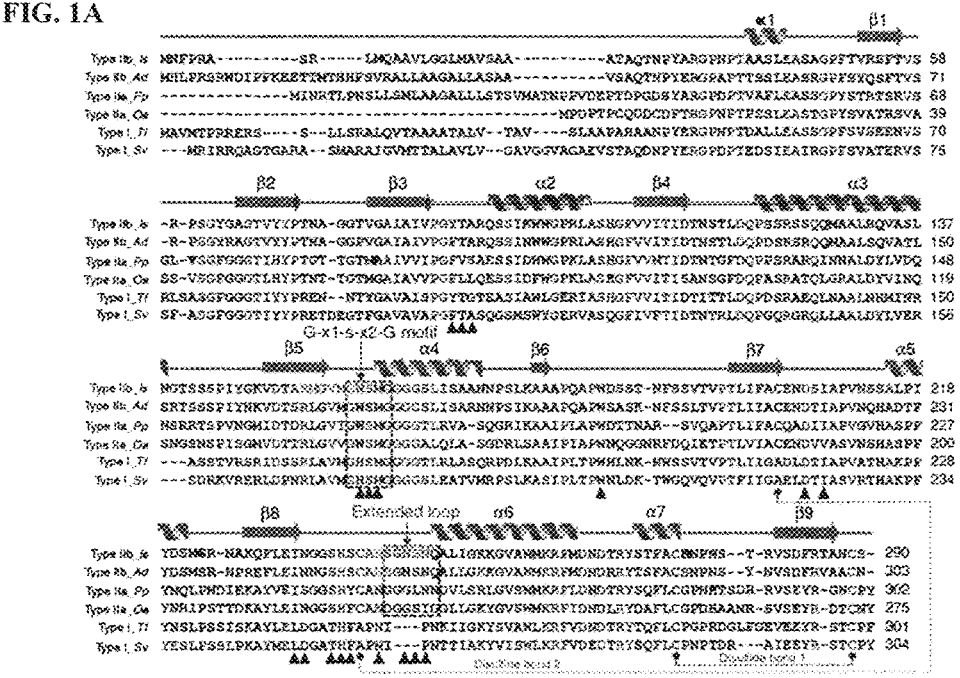
FIG. 1A shows an alignment of the amino acid sequence of the PET-decomposing enzyme. Amino acid sequences of two types I, two types IIa, and two types IIb, that is, six different PET-decomposing enzymes are compared. Secondary structural elements are indicated based on the IsPETase structure and are indicated using arrows (β-sheet) and helix (α-helix). Gly-x1-Ser-x2-Gly motif and extended loop are highlighted using boxes. Residues related to enzyme catalysis and configuration of a sub-site I and a sub-site II are shown in triangles, respectively. Disulfide-bonds found in all six enzymes are indicated by an line and 'disulfide-bond 1'. Additional disulfide-bonds found only in the IsPETase are indicated by the line and 'disulfide-bond 2'. Is, Ad, Pp, Oa, Tf, and Sv respectively refer to *Ideonella sakaiensis, Acidovorax delafieldii, Pseudomonas pseudoalcaligenes, Oleispira Antarctica, Thermobifida fusca,* and *Saccharomonospora viridis* based PET-decomposing enzymes.
Figure 1B:
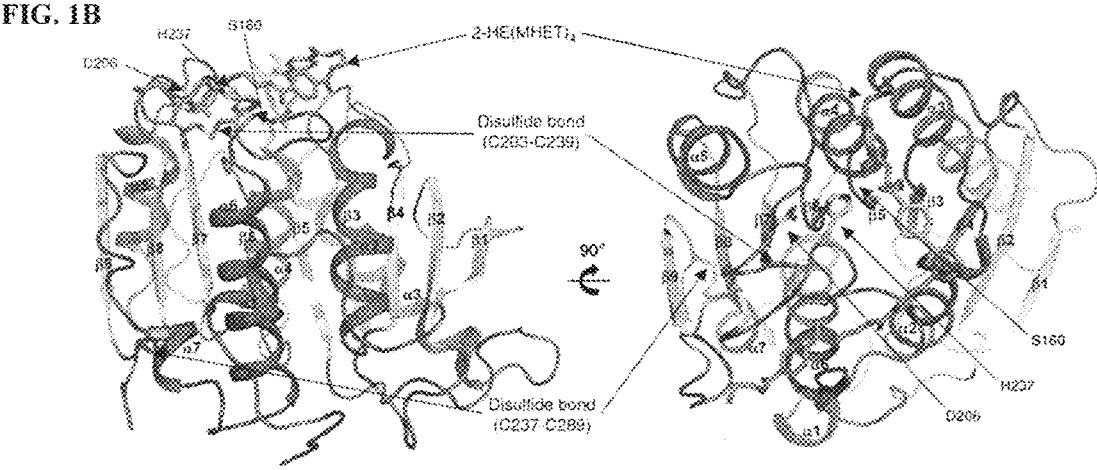
FIG. 1B shows the IsPETase structure. The monomer structure is represented via a ribbon diagram. The three residues of Ser160, Asp206 and His237 forming the catalyst triplet are denoted as sticks and the two disulfide-bonds are denoted as sticks. The 2-HE(MHET)$_4$ molecule simulated at the active site is represented by an stick. The drawing on the right results from a 90 degrees rotation of the drawing on the left in a horizontal direction.
Figure 2A:
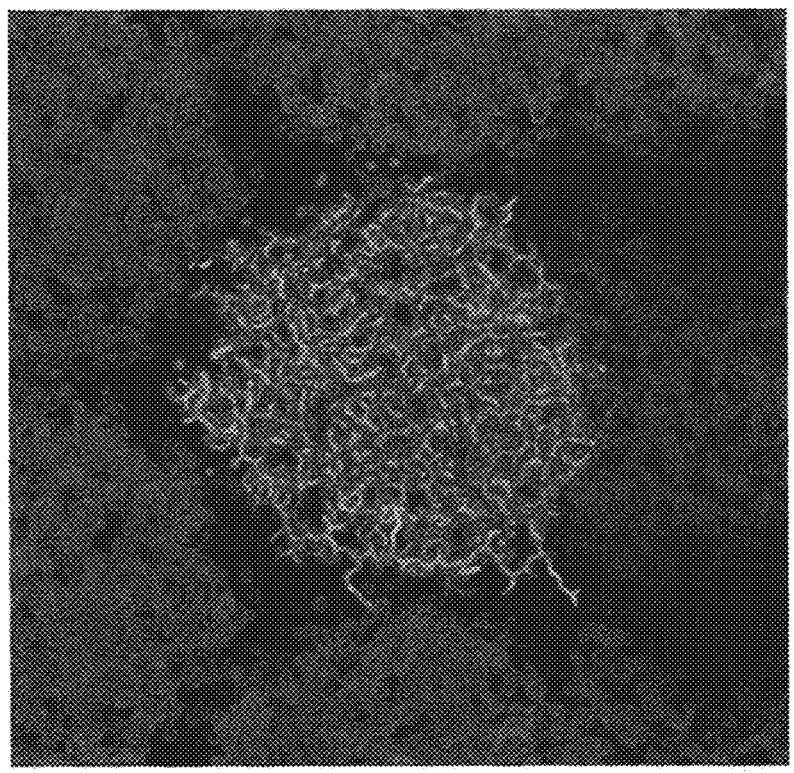
FIG. 2A shows the electron density map of the IsPETase, which is produced through WinCoot. The 2F$_0$-F$_c$ map outlined at 1.5σ is indicated using a mesh. The no crystal symmetry suggests the monomer structure of the IsPETase.
Figure 2B:
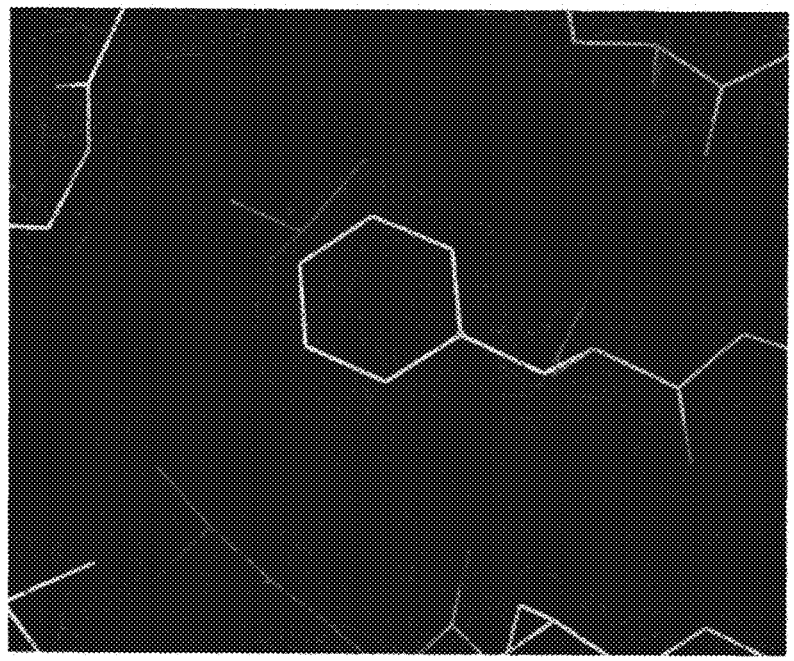
FIG. 2B shows the IsPETase structure at a high resolution of 1.0 Å.
Figure 4:
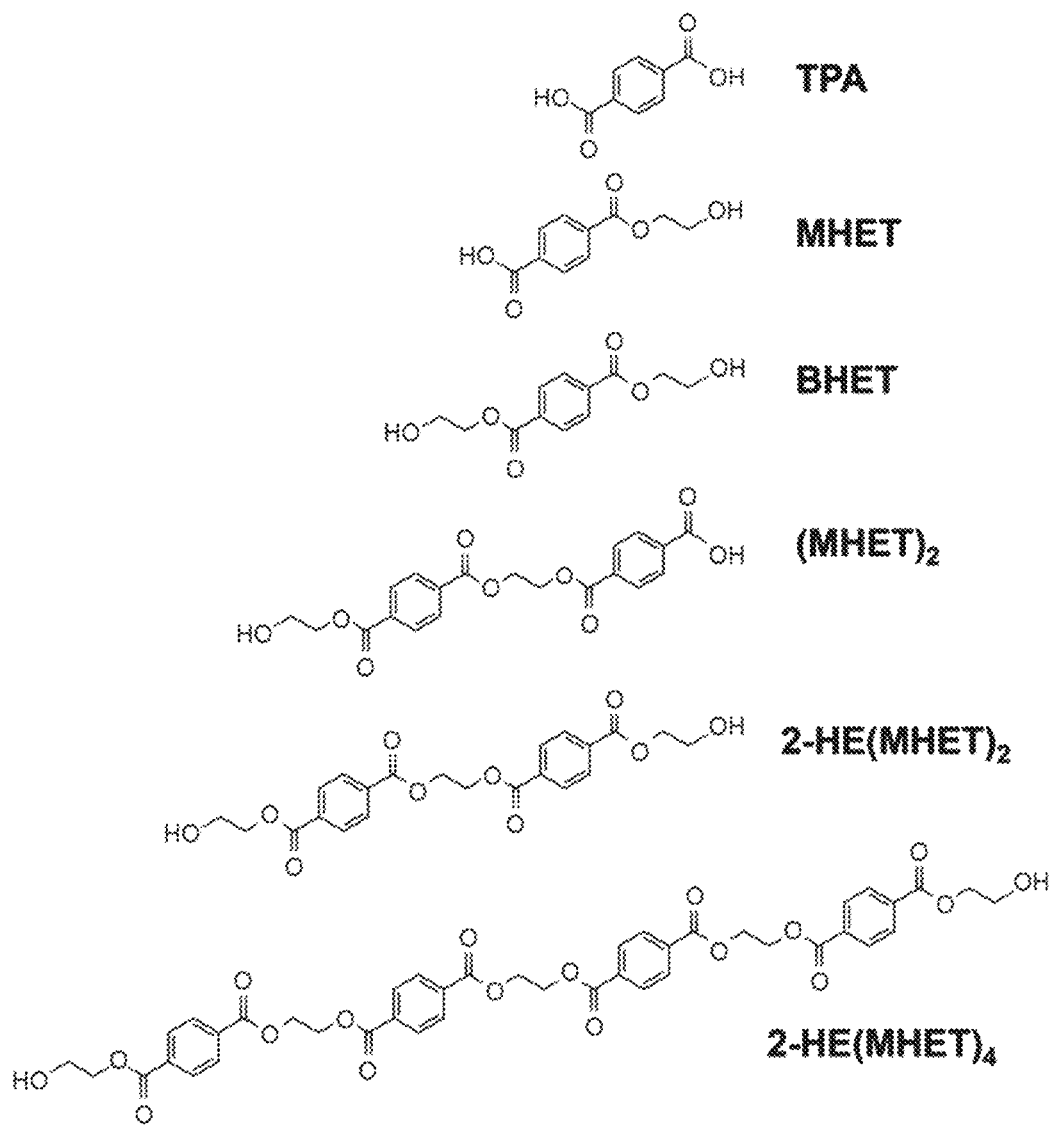
FIG. 4 shows chemical structures of PET-related molecules.

Hereinafter, the present invention will be described in more detail by the following Examples. However, the Examples are intended to illustrate the present invention only, and the scope of the present invention is not limited thereto.

Example 1. Production of IsPETase Protein

For IsPETase expression in *Escherichia coli* cells, the IsPETase gene was amplified by polymerase chain reaction (PCR) using a codon-optimized synthetic gene as a template. The nucleotide sequence corresponding to the signal peptide was removed from the synthetic DNA. Then, The PCR product was subcloned into vector pET 15b. Using the thus produced expression vector pET 15a: IsPETase, E. coli strain Resettagami-B was transformed. The E. coli strain Resettagami-B was grown in 1 L of lysogeny broth medium containing ampicillin at 37° C. Protein expression was induced via addition of 1 mM isopropyl β-D-1-thiogalacto-pyranoside, and then, the culture medium was further cultured at 18° C. for 16 hours. The medium centrifuged at 4000×g for 10 minutes at 20° C. The cell pellet was resuspended in a buffer A (50 mM Tris-HCl, pH 8.0) and then was crushed with ultrasound treatment. Resulting cell debris was removed by centrifugation at 13500×g for 25 minutes. The supernatant was applied to a Ni-NTA agarose column (Qiagen). After washing with a buffer A containing 30 mM imidazole, the binding protein was eluted with 300 mM imidazole in the buffer A. Finally, traces of contaminated substances were removed by size-exclusion chromatography using a Superdex 200 prep-grade column (320 ml, GE Healthcare) equilibrated with the buffer A. All purification steps were performed at 4° C. Protein purity was determined by sodium dodecyl sulfate polyacrylamide gel electrophoresis. The purified protein was concentrated to 28 mg/ml in 50 mM $Na_2HPO_4$—HCl (pH 7.0) and 100 mM NaCl.

Example 2. IsPETase Protein Crystal

Example 2-1. Production of IsPETase Protein Crystal

Crystallization of the purified IsPETase protein was performed using a crystal screening kit: Index and PEG/Ion (Hampton Research) and Wizard I and II (Rigaku) based on a hanging-drop vapor diffusion method at 20° C. Each experiment was conducted using 1.0 μl of a protein solution and 1.0 μl of a reservoir solution and then equilibrated with 50 μl of a reservoir solution.

The highest quality IsPETase crystals were found when using 0.1M ammonium acetate, 0.1M bis-tris (pH 5.0) and 17% polyethylene glycol 10000. The protein crystal was transferred to a cryoprotectant solution containing 0.1M ammonium acetate, 0.1M bis-tris (pH 5.0), 20% polyethylene glycol 10,000 and 30% (v/v) glycerol. Then, the protein crystal was extracted using a loop larger than the crystal, and was immersed in the liquid nitrogen, and was rapidly frozen therein.

Example 2-2. X-Ray Diffraction Analysis of IsPETase Protein Crystal

Data were collected at 100K via Beamline 6D from the Pohang Accelerator Laboratory (Pohang, Korea) for the analysis of the IsPETase protein crystal. The data were indexed and integrated and scaled using the HKL2000 software suite. Thus, it was confirmed that the IsPETase crystal belongs to a space group $P2_12_12_1$, and that the IsPETase crystal has unit cell parameters a=43.48 Å, b=50.40 Å, and c=129.49 Å. For one molecule of IsPETase on an asymmetric unit basis, the Metthews modulus was 2.64 Å$^3$/Da, which corresponds to a solvent content of 53.38%.

Example 2-3. Determination of Structure of IsPETase Protein Crystal

In order to characterize the structure of the IsPETase protein crystal, *Thermobifida alba* (TaCut, PDB code 3VIS, 50% sequence identity)-derived cutinase structure was employed as a search model. Then, we have identified the structure of the IsPETase via the molecular substitution method using the CCP4 version of MOLREP. Then, a model building was performed using the WinCoot program. Purification was carried out using REFMAC5. The statistical data are shown in Table 1. The refined model of the IsPETase is stored in Protein Data Bank as PDB code 5XJH.

TABLE 1

|  | IsPETase | IsPETase$^{R280A}$ |
| --- | --- | --- |
| PDB code | 5XJH | 5YNS |
| Data collection |  |  |
| Wavelength (Å) | 0.97934 | 0.97934 |
| Unit cell (a, b, c; γ) (Å; °) | 43.48, 50.40, 129.49; 90.0 | 43.61, 50.59, 129.58; 90.0 |
| Space group | $P2_12_12_1$ | $P2_12_12_1$ |
| Solvent content (%) | 53.38 | 52.66 |
| Protein chains in AU | 1 | 1 |
| Resolution range (Å) | 50.00-1.55 | 50.00-1.36 |
| Highest resolution shell (Å) | 1.58-1.55 | 1.38-1.36 |
| Unique reflections | 42939 | 62434 |
| Redundancy | 6.5 (5.9) | 9.3 (5.7) |
| Completeness (%) | 99.9 (99.9) | 98.7 (96.9) |
| $R_{merge}$ (%) | 6.8 (29.8) | 6.7 (30.1) |
| Average I/σ (I) | 31.4 (5.2) | 40.8 (4.6) |
| B from Wilson plot (Å$^2$) | 14.2 | 10.8 |
| Refinement |  |  |
| R (%) | 15.9 | 16.6 |
| $R_{free}$ (%) | 19.2 | 19.2 |
| Mean B value (Å$^2$)* | 16.1 | 15.0 |
| RMS deviation bond lengths (Å) | 0.026 | 0.025 |
| RMS deviation bond angles (°) | 2.286 | 2.249 |
| Number of amino acid residues | 272 | 264 |
| Number of water molecules | 150 | 294 |
| Ramachandran plot |  |  |
| Most favored regions (%) | 97.3 | 97.6 |
| Additional allowed Regions (%) | 2.7 | 2.4 |

*Mean B value is for both protein atoms and the solvent molecules.

The signal peptide sequence (Met1-Ala33) was removed for production of the protein core domain. Recombinant IsPETase protein has additional amino acid residues at both the N and C terminals (Met13-Met33 and Leu291-Gln312) due to the use of the pET 15b vector.

As a result, the IsPETase crystal structure was determined at 1.5 Å resolution (FIGS. 1A and 1B and FIGS. 2A and 2B). The structure includes the Ser31-Gln292 residue, which may be seen in the electron density map. The refined structure is consistent with X-ray crystallographic statistics in terms of a binding angle, a bind length, and other geometric parameters (See Table 1). The asymmetric unit of the space group $P2_12_12_1$ includes one molecule of IsPETase. This indicates that the IsPETase exists as a monomer. The IsPETase crystal structure belongs to the α/β hydrolase superfamily. The central twisted β-sheet is composed of nine mixed β-strands (β1 to β9) and is surrounded by seven α-helix (α1 to α7) (See FIG. 1B). As observed in proteins belonging to other α/β hydrolase superfamilies such as lipase and estrase, the IsPETase contains a conserved serine hydrolase Gly-x1-Ser-x2-Gly motif (Gly158-Trp159-Ser160-Met161-Gly162) located in the active site (See FIG. 1A).

Example 2-4. Active Site of IsPETase Protein Crystal

The IsPETase decomposes a PET into monomers such as bis(2-hydroxyethyl) terephthalate (BHET), mono(2-hydroxyethyl) terephthalate (MHET) and terephthalic acid (TPA) (See FIG. 3A-3D). Further, the IsPETase hydrolyzes BHET widely used in PET studies as a monomer that is similar to the core structure of the PET and is commercially available. BHET is decomposed into MHET by the IsPETase without further decomposition reaction. Covalent bond based docking calculation was executed using 2-hydroxyethyl-(monohydroxyethyl terephthalate)$_4$, 2-HE (MHET)$_4$ and 4-MHET molecules mimicking the PET to estimate a binding manner of the enzyme to the substrate (See FIG. 3A-3D).

Tetrahedral intermediate molecular docking from 2-HE (MHET)$_4$ to an IsPETase structure was performed through a hybrid approach of soft and covalent bond based dockings using AutoDock 4.2 and AutoDock Vina. The ligand molecules of IsPETase were prepared with WinCoot and ProDrg. The nonpolar H atoms were merged into both the ligand and target using AutoDock Tools prior to the docking. Soft residues (Tyr87, Trp159, Ser160, Met161, Trp185, Ile208, His237, Ser238, and Asn241) were selected for the production of the pdbqt file of both hard and soft receptors. The bonds to the side-chains of the residues were allowed for rotation. A grid box is centered at x: −3.249, y: 25.239 and z: −29.093. The box size has axis lengths 90.7, 74.7, and 122.7 Å, respectively. Prior to the covalent bond based docking, non-covalent bond based docking calculations were performed using AutoDock Vina. Nine output poses occurred with a binding free energy as calculated from the scoring function thereof. We chose the best docking model with the lowest binding energy (−7.1 kcal/mol). A conformation of the model was used as an evaluation criterion for following calculations. Further, an induced conformation of the soft residue in the best model was applied to receptors for the covalent bond based docking. A total of 200 docking poses were evaluated based on the appropriate distance of the oxygen anion hole. The best pose with the binding energy −10.27 kcal/mol (from a semi-empirical free energy force field of AutoDock) was similar to the non-covalent bond based docking result. Finally, the docking pose was minimized using the OPLS3 force field in the Schrodinger suite.

It has been shown that at the active site of the IsPETase protein, three residues Ser160, His237, and Asp206 form a catalytic triplet, and a residue Ser160 functions as a covalent bond nucleophile with respect to the carbonyl carbon atom of a cleavable ester bond, such as a carboxyl esterase (See FIG. 3A). A tetrahedral intermediate oxygen anion was stabilized by an oxygen anion hole composed of nitrogen atoms of Tyr87 and Met160 having respectively distances of 2.90 and 2.83 Å(See FIG. 3A). The substrate-binding site was simulated to form a long and shallow L-shaped gap in a flat surface with values of approximately 25 and 29 Å (See FIG. 3B-3D). A surface of the substrate-binding gap was mainly hydrophobic and a length of the gap was ~40 Å (See FIG. 3B). Based on the cleavable ester bond of the 2-HE (MHET)$_4$, the substrate-binding site may be divided into two sub-sites, that is, a sub-site I and a sub-site II, onto which one and three MHET moieties are combined respectively (See FIGS. 3B & 3E). For binding of a first MHET moiety in the sub-site I, a benzene ring is located at a valley between two aromatic residues Tyr87 and Trp185 (See FIGS. 3B & 3E). A π-π interaction between the benzene ring of the first MHET moiety and the Trp185 with a distance of ~3.6 Å appears to be a major factor for ligand stabilization (See FIG. 3E). Further, Met161 and Ile208 are predicted to aid binding of the first MHET moiety by providing hydrophobic surfaces at a bottom and sides of the sub-site I respectively (See FIG. 3E). The sub-site II tends to form a longer and shallow gap than that defined in the sub-site I. The sub-site II accommodates three MHET moieties (second, third and fourth MHET moieties of the 2-HE(MHET)$_4$) (See FIG. 3B-3D). Based on a MHET binding, the sub-site II is further subdivided into three sub-sites IIa, IIb, and IIc (See FIGS. 3B & 3E). The sub-site II is composed of residues including Thr88, Ala89, Trp159, Ile232, Asn233, Ser236, Ser238, Asn241, Asn244, Ser245, Asn246, and Arg280. An interaction between the sub-site II and the 2 MHET moieties appears to be mediated primarily via a hydrophobic interaction. However, a carbonyl oxygen atom of the fourth MHET moiety forms a polar interaction with the Ser236 main chain and Asn246 side chain within the sub-site IIc (See FIGS. 3B & 3E). The residue Arg280 is located at an end portion of the sub-site IIc, and the residue Arg280 is positively charged and has a slightly protruding structure that interferes with extension of the substrate-binding site (See FIGS. 3B, 3C, & 3E).

Example 3. IsPETase Variant

Example 3-1. Production of IsPETase Variant Protein

Site-directed mutagenesis experiments were conducted to determine residues associated with enzyme catalysis and substrate binding. The site-directed mutagenesis experiments were performed using a Quick Change kit (Stratagene). Expression and purification of the IsPETase variant were performed under the same condition as the expression and purification of the IsPETase protein.

Example 3-2. Production of IsPETase Variant Protein Crystal

Crystallization of the IsPETase variant Protein was performed by a method similar to a method of the crystallization of IsPETase protein in the above Example 2-1.

Example 3-3. X-Ray Diffraction Analysis of IsPETase Variant Protein Crystal

Data were collected at 100K via Beamline 7A from the Pohang Accelerator Laboratory (Pohang, Korea). As a result, IsPETase$^{R280A}$ crystal belongs to the space group P2$_1$2$_1$2$_1$, and unit cell parameters were similar to those in the IsPETase$^{W/T}$ crystal.

Example 3-4. Determination of Structure of IsPETase Variant Protein Crystal

A structure of IsPETase$^{R280A}$ was identified via a molecular substitution method using an IsPETase$^{W/T}$ structure as a search model. Modeling and purification were performed in the same manner as in the IsPETase$^{W/T}$ in the Example 2-3. The statistical data are shown in Table 1. The refined model of IsPETase$^{R280A}$ is stored in the Protein Data Bank as PDB code 5YNs.

Example 4. Activity Analysis

Example 4-1. In Vitro Analysis Using Bis-Hydroxyethyl Terephthalate

For comparison of activities, bis-hydroxyethyl terephthalate (BHET) was used as a substrate for enzyme analysis. A BHET stock solution was prepared by dissolving (2.5 g/l) BHET in dimethyl sulfoxide. The analysis protocol was based on a previously reported article (Yosida, S. et al. Science 351, 1196-1199, 2016). Enzyme assays were performed using 200 mg/l BHET in a buffer solution (80 mM $Na_2HPO_4$—HCl, 40 mM NaCl) at pH 7.0. The enzyme reaction was initiated by addition of 50 nM enzyme thereto and lasted for 30 minutes at 30° C. Then, after heating at 85° C. for 15 minutes, the reaction was terminated. The reaction mixture was centrifuged at 13,200 r.p.m. for 10 minutes. Finally, the supernatant was subjected to liquid chromatography (LC) analysis.

In vitro assay samples were analyzed by HPLC (1100 Series HPLC, Agilent) equipped with MS LC/MSD VL, Agilent). An Eclipse Plus-C18 column (5 μm, 4.6×150 mm, Agilent) was used. All analyzes were performed at a room temperature (25° C.). For a mobile phase, a buffer A (0.1% formic acid in distilled water) and a buffer B (acetonitrile) were used at a flow rate of 0.8 ml/min. The mobile phase was gradually changed from a 95% buffer A to a 30% buffer A in 20 minutes (all % means volume %). Chemical substances (BHET, MHET and TPA) were detected at 260 nm.

Figure 5A:
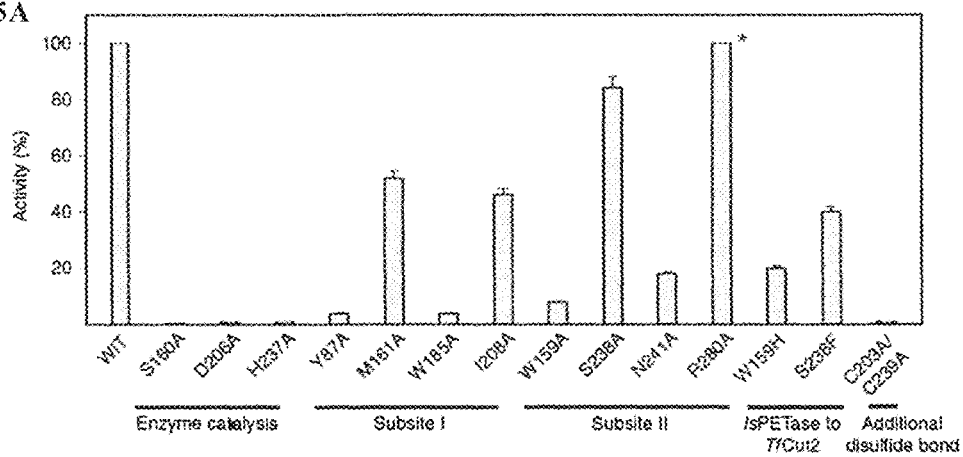
FIG. 5A shows hydrolysis activity of the IsPETase and its variants when using BHET as a substrate. The PETase activities of the IsPETase and its variants are measured with a concentration of 200 mg/L of BHET and enzyme concentration of 50 nM. The amount of MHET as produced is monitored by HPLC analysis. The PETase activity of the IsPETase variant is compared with that of the IsPETase wild-type.

Catalytic residues Ser160, Asp206 and His237 were substituted with Ala and then hydrolysis activity was measured using BHET as a substrate. All three variants $IsPETase^{S160A}$, $IsPETase^{D206A}$ and $IsPETase^{H232A}$ show nearly complete loss of the activity (See FIG. 5A). This indicates that these three residues are involved in catalysis.

Subsequently, Tyr87, Trp185, Met161, and Ile208 residues, which constitute the sub-site I, were substituted with Ala. $IsPETase^{Y87A}$ and $IsPETase^{W188A}$ variants exhibited 5% BHET hydrolysis activity compared to the $IsPETase^{W/T}$ (See FIG. 5A). This result implies that blocking the π-π interaction between these residues and the benzene ring of the first MHET moiety reduces the stability of the first MHET moiety. $IsPETase^{M181A}$ and $IsPETase^{I208A}$ variants show 52% and 46% activities, respectively, compared to $IsPETase^{W/T}$ (See FIG. 5A). This means that this residue is not as important as the Tyr87 and Trp185 residues but contributes to the constitution of the sub-site I.

The residues Trp159, Ser238, and Asn241 that constitute the sub-site II were substituted with Ala. $IsPETase^{W159A}$ and $IsPETase^{M241A}$ showed 8% and 18% BHET hydrolysis activities respectively compared to $IsPETase^{W/T}$ (See FIG. 5A). This means that this residue is important in the constitution of the sub-site II. However, $IsPETase^{S238A}$ showed an almost similar activity of BHET hydrolysis compared to $IsPETase^{W/T}$ (See FIG. 5A). This result suggests that substitution of the Ser238 with Ala does not affect the BHET hydrolysis activity of the enzyme.

Example 4-2. In Vitro Analysis Using PET Film

The analysis was carried out with minor modifications (as described below) based on the previously reported article (Yosida, S. et al. Science 351, 1196-1199, 2016). In order to analyze the decomposition rate of the PET by the PETase, a commercially available PET film (UBIGEO, Korea) was used as a substrate for enzyme analysis. The PET film was prepared in a circular shape having a diameter of 6 mm. The PET film was wetted with 300 μl of pH 9.0 glycine-NaOH buffer and 200 nM the enzyme. The reaction mixture was incubated at 30° C. for 18 and 36 hours/24 and 72 hours. After heating at 85° C. for 15 minutes, the reaction was terminated. Thereafter, the sample was centrifuged at 13,200 r.p.m. The supernatant was analyzed via LC. After the enzymatic reaction, the film was washed with 1% SDS and 20% ethanol in distilled water.

Figure 5B:
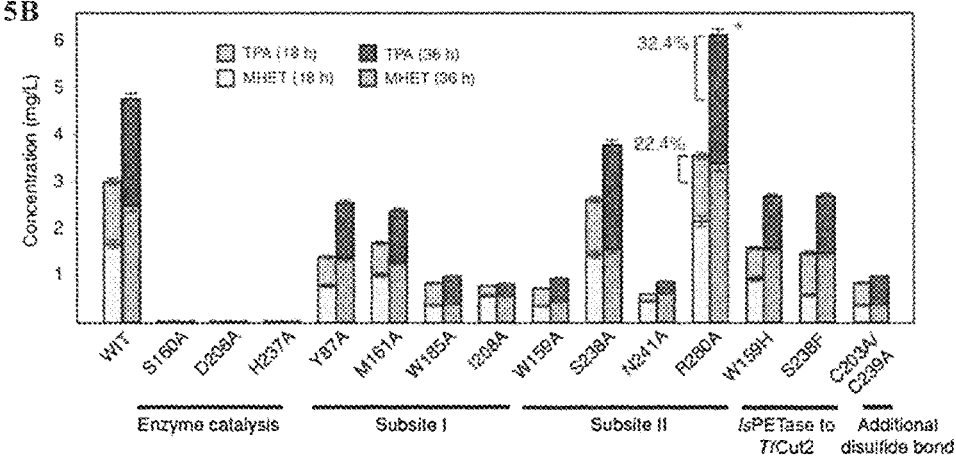
FIG. 5B shows PETase activity of the IsPETase protein when using a PET film as a substrate. The decomposition activity of the PET film by the IsPETase protein is measured with an enzyme concentration of 200 nM. The amounts of thus produced MHET and TPA are monitored by HPLC analysis. The PETase activity of the IsPETase variant is compared with that of the IsPETase wild-type. The IsPETase$^{R280A}$ variant, which exhibits the increased activity, is highlighted as a star.
Figure 5C:
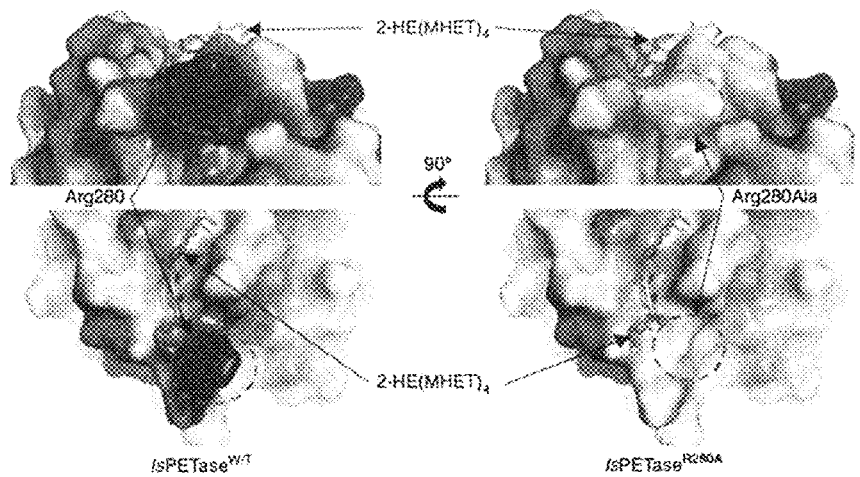
FIG. 5C shows the electrostatic potential surface of the IsPETase$^{R280A}$ structure. 2-HE (MHET)$_4$ molecules are labelled. Arg280 residue in IsPETas$^{W/T}$ and Arg280Ala(R280A) residue in IsPETase$^{R280A}$ are indicated by dotted circles. The error bars represent the standard deviation values obtained in duplicate experiments.

The PETase activity of the variant was measured when using a PET film as a substrate. The variant of the catalyst triplet with Ala showed an almost loss of the enzyme activity. The variant involved in the configuration of the substrate-binding site showed decreased PETase activity compared to the $IsPETase^{W/T}$ (See FIG. 5B). The substitution of Arg280 with Ala was preformed and then the BHET hydrolysis and PETase activity were measured. The $IsPETase^{R280A}$ showed an almost similar activity to that of $IsPETase^{W/T}$ (See FIG. 5A). When a PET film is used as a substrate, the $IsPETase^{R280A}$ was found to increase the PETase activity by 22.4% at 18 h and by 32.4% at 36 h (See FIG. 5B) compared to the $IsPETase^{W/T}$ (high specificity of IsPETase to PET). In other words, substitution of Arg280 with a small hydrophobic residue enables a more stable binding of the longer substrate, thus resulting in an increase in the PETase activity. More specifically, to investigate whether the substitution of Arg280 with Ala actually changed the conformation of the substrate-binding site (the sub-site IIc) to enable the binding of the longer substrate, the structure of $IsPETase^{R280A}$ was checked at 1.36 Å resolution. As expected, the structure of $IsPETase^{R280A}$ exhibited an extended sub-site IIc by providing a hydrophobic and non-protruding gap, compared to the $IsPETase^{W/T}$ (See FIG. 5C). Substitution of Arg280 at a terminal from a catalyst site with a distance of 22.8 Å with Ala could also be known to increase the enzyme activity. This result could not be obtained without reliable docking calculations to check the inherent binding properties of the IsPETase to the substrate.

Figure 6:
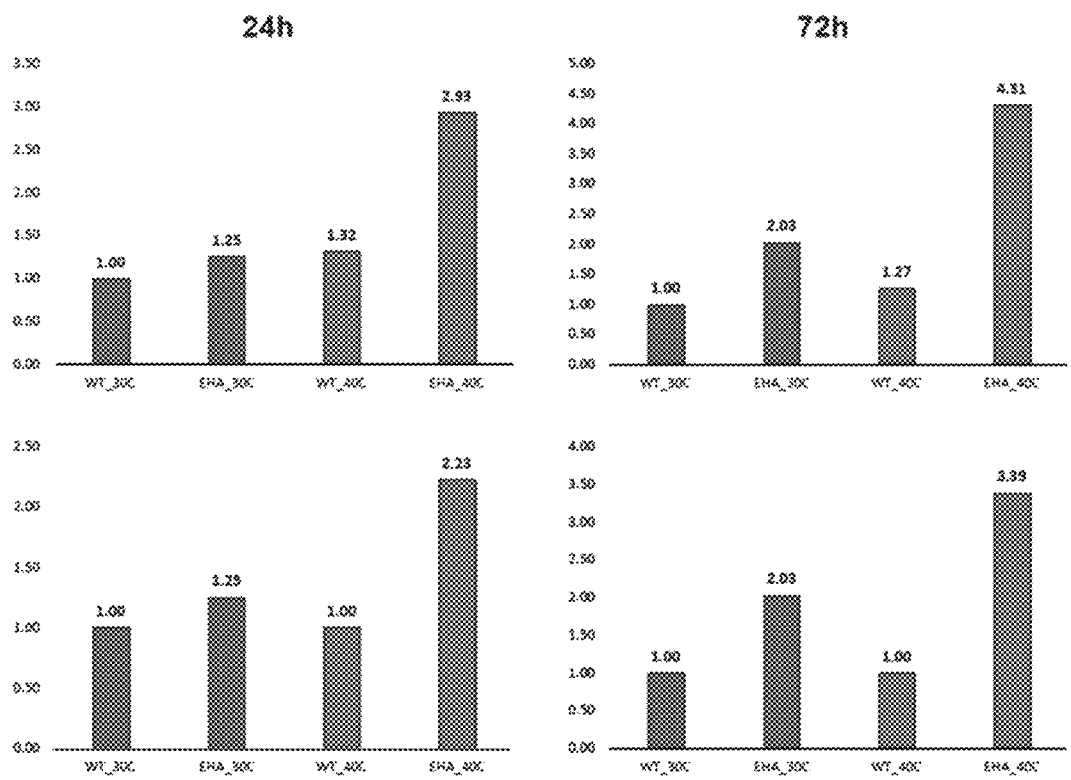
FIG. 6 shows the PETase activity of the IsPETase$^{S121E/D186H/R280A}$ variant. The hydrolysis activities of the IsPETase and its variants are measured when using the PET film as a substrate. The PETase activity of the IsPETase$^{S121E/D186H/R280A}$ variant is measured at an enzyme concentration of 200 nM. The amount of MHET as produced is monitored by HPLC analysis. The PETase activities at 24 hours and 72 hours of IsPETase$^{S121E/D186H/R280A}$ variants are compared with those of IsPETase$^{W/T}$ at 30° C. and 40° C.

The PETase activity was measured by substitution of Ser121 with Glu, Asp186 with His, and Arg280 with Ala. When using the PET film as a substrate, $IsPETase^{S121E/D186H/R280A}$ has the PETase activity increased by 1.25 times at 30° C. and 2.23 times at 40° C. at 24 hours and by 2.03 times at 30° C. and 3.39 times at 40° C. at 72 hours compared with the $IsPETase^{W/T}$ (See FIG. 6). The hydrogen bond resulting from the substitution increased the stability of the enzyme and consequently increased the PETase activity. The increased stability of the enzyme may be confirmed via the increase in the melting point (Tm) of the enzyme. From this fact, we could know that the S121E and D186H substitutions in the IsPETase variant individually increased the PETase activity or increased the PETase activity synergistically in combination with other substitutions.

Example 5. Activity Analysis of IsPETase Protein about Thermal Stability

Example 5-1. Thermal Stability Site of IsPETase Protein Crystal

Figure 7A:
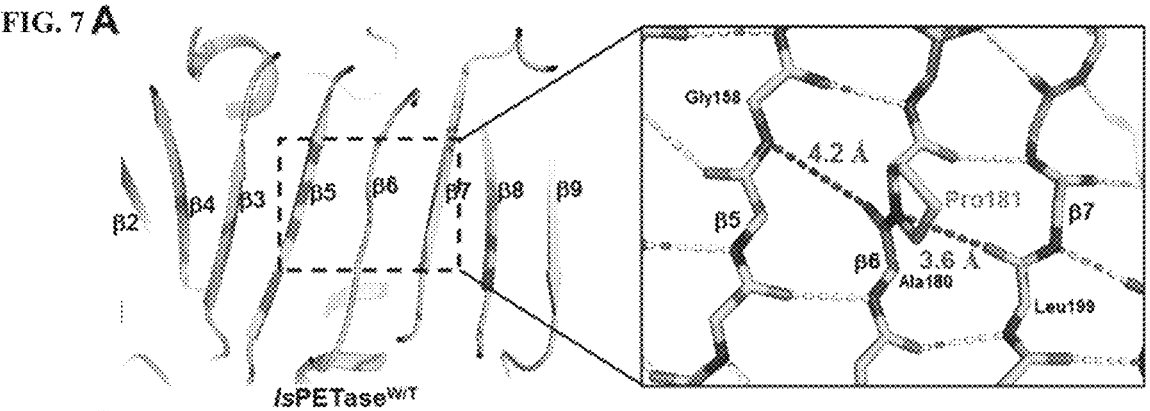
FIG. 7A shows that a central twisted β-sheet of IsPETase$^{W/T}$ is composed of nine mixed β-strands (β1 to β9). The hydrogen-bonds formed by nitrogen and oxygen respectively are indicated by dotted lines.
Figure 7B:
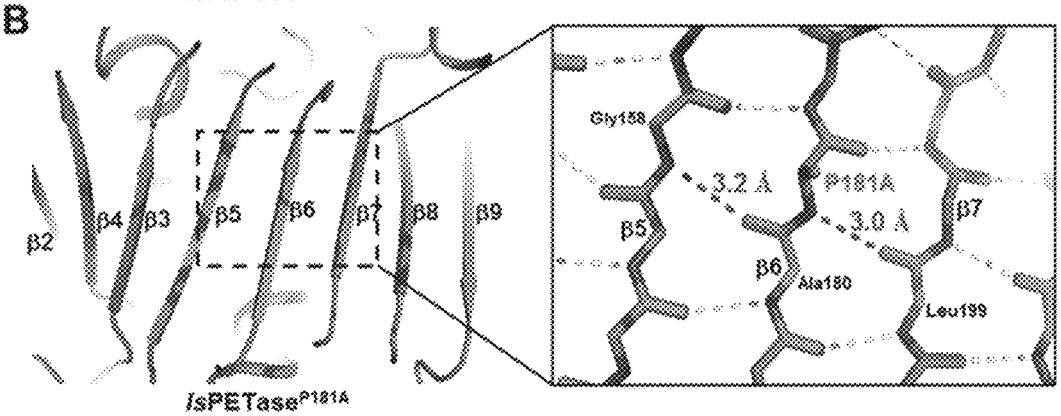
FIG. 7B shows that the central twisted β-sheet of IsPETase$^{P181A}$ variant is composed of nine mixed β-strands (β1 to β9). The hydrogen-bonds formed by nitrogen and oxygen respectively are indicated by dotted lines.
Figure 7C:
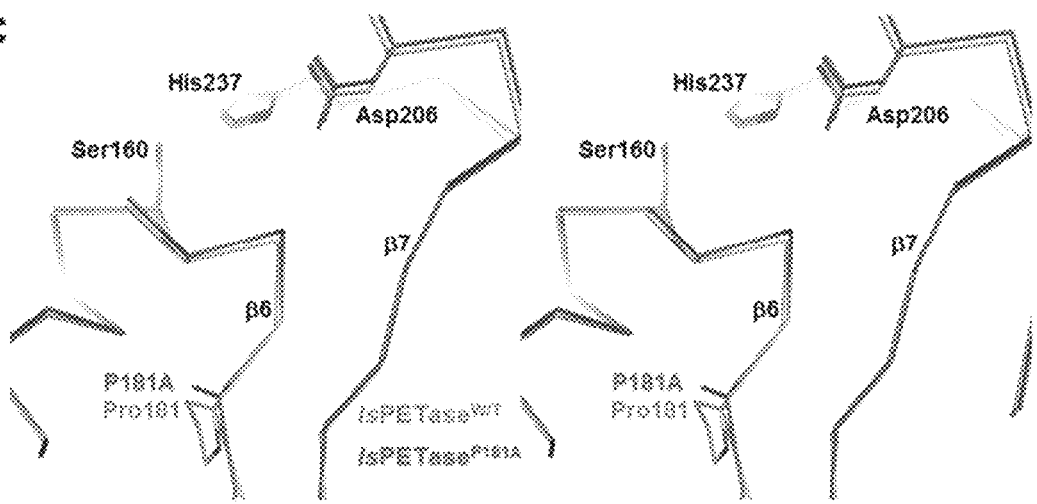
In FIG. 7C, a structure of the IsPETase$^{W/T}$ or the IsPETase$^{P181A}$ are indicated by a line.

The IsPETase has the superior PET decomposition activity compared to other PET-decomposing enzymes. However, due to its low thermal stability, the IsPETase has the disadvantage that it may be used to decompose the PET only at a moderate temperature (30° C.). Thus, the thermal stability of the IsPETase is predicted to be a critical factor in the efficient decomposition of the PET using the PETase. Thus, structural properties that affect the thermal stability of the IsPETase protein crystal were determined (See FIG. 7A-7C).

As a first structural feature, the IsPETase crystal has an unusual conformation of a β6-sheet. In other words, the Pro181 residue located at the center of the β6-sheet in the IsPETase crystal does not form a hydrogen bond with adjacent amino acids, thus interfering with the formation of continuous β-sheet. In the structure of the IsPETase crystal, a distance between nitrogen of the Pro181 residue and oxygen of the Leu199 residue is 3.6 Å, and a distance between nitrogen of Gly158 residue and oxygen of Ala180 residue is 4.2 Å. This suggests that the Pro181 residue interferes with the secondary structure formation of the IsPETase protein (See FIG. 7A).

Figure 8A:
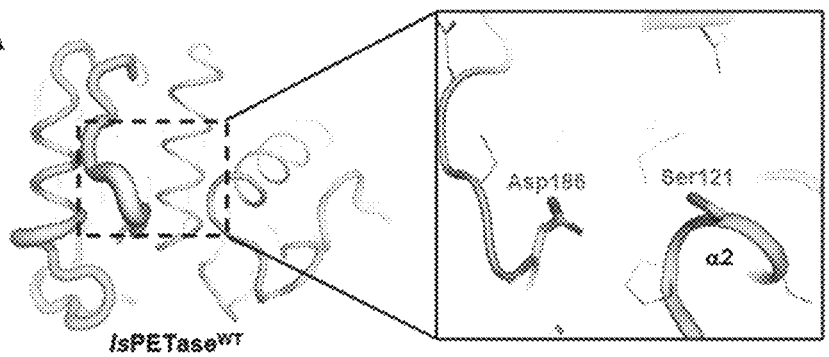
FIG. 8A shows the β6-β7 connection loop (Asp186-Phe191) and adjacent α-helix Ser121 residue of the IsPETase$^{W/T}$.
Figure 8B:
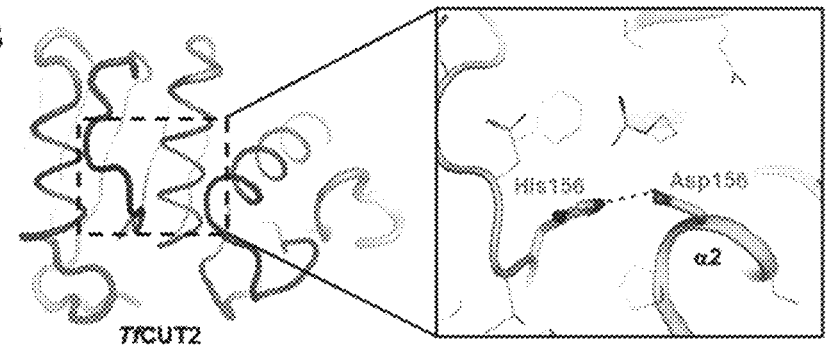
FIG. 8B shows the β6-β7 connection loop (His156-Trp161) of *Thermobifida fusca* DSM43793-derived TfCut2 and adjacent α-helix Asp156 residue thereof. The hydrogen-bonds formed by nitrogen and oxygen respectively are indicated by dotted lines.

As a second structural feature, the β6-β7 connecting loop (Asp186-Phe191) in the IsPETase crystal has a higher b-factor value (22.2) than an average b-factor value (16.1) in the entire protein and has a very flexible structure (See FIG. 8A). On the other hand, in *Thermobifida fusca* DSM43793-derived cutinase2(TfCut2), which has a high thermal stability, the β6-β7 connecting loop (His156-Trp161) has a b-factor value similar to the average b-factor of the entire protein and has a very flexible structure (See FIG. 8B). In this connection, the His156 residue seems to contribute to the structural stability of the connection loop by the His156 residue forming a hydrogen bond with an Asp156 residue in a α2-helix. Therefore, the substitution of Asp186 and Ser121 residues of the IsPETase crystal with histidine and aspartic acid, respectively, as in the TfCut2 may allow the hydrogen bonds to be formed in the β6-β7 connection loop, resulting in the improved structural stability.

Example 5-2. Production of IsPETase Variant Protein

Site-directed mutagenesis experiments were performed to determine the amino acid residues of the IsPETase associated with thermal stability. The site-directed mutagenesis experiments were performed under the same conditions as in the Example 3-1. Thus, $\text{IsPETase}^{S121D}$, $\text{IsPETase}^{S121E}$, $\text{IsPETase}^{D186H}$, $\text{IsPETase}^{D186F}$, $\text{IsPETase}^{D186I}$, $\text{IsPETase}^{D186L}$, $\text{IsPETase}^{D186V}$, $\text{IsPETase}^{S121D/D186H}$, $\text{IsPETase}^{S121E/D186H}$, $\text{IsPETase}^{P181A/S121E/D186H}$, $\text{IsPETase}^{P181A/S121E/D186H}$, $\text{IsPETase}^{S121D/D186H/R280A}$, and $\text{IsPETase}^{S121E/D186H/R280A}$ were produced. Further, the crystallization of the IsPETase variant protein was performed under the same conditions as in the Example 3-2.

Structures of $\text{IsPETase}^{S121D/D186H}$, $\text{IsPETase}^{S121E/D186H}$ and $\text{IsPETase}^{S121E/D186H/R280A}$ were identified via a molecular substitution method using the $\text{IsPETase}^{W/T}$ structure as a search model. Modeling and purification were performed under the same conditions as in the $\text{IsPETase}^{W/T}$ in the Example 2-3. Statistical data are shown in Table 2 below. Refined models of the $\text{IsPETase}^{S121D/D186H}$, $\text{IsPETase}^{S121E/D186H}$ and $\text{IsPETase}^{S121E/D186H/R280A}$ are stored in Protein Data Bank as PDB codes 6IJ3, 6IJ4, 6IJ6, respectively.

TABLE 2

|  | $\text{IsPETase}^{S121D/D186H}$ | $\text{IsPETase}^{S121E/D186H}$ | $\text{IsPETase}^{S121E/D186H/R280A}$ |
|---|---|---|---|
| PDB code | 6IJ3 | 6IJ4 | 6IJ6 |
| Data collection | | | |
| Wavelength (Å) | 0.97934 | 0.97934 | 0.97934 |
| Unit cell (a, b, c; γ) (Å; °) | 115.43, 50.63, 41.49; 90.0, 93.1, 90.0 | 116.20, 50.86, 41.49; 90.0, 92.7, 90.0 | 114.91, 51.14, 51.16; 90.0, 109.7, 90.0 |
| Space group | C121 | C121 | C121 |
| Solvent content (%) | 47.20 | 47.80 | 54.84 |
| Protein chains in AU | 1 | 1 | 1 |
| Resolution range (Å) | 50.00-1.40 | 50.00-1.85 | 50.00-1.95 |
| Highest resolution shell (Å) | 1.42-1.40 | 1.88-1.85 | 1.98-1.95 |
| Unique reflections | 46596 | 19977 | 19893 |
| Redundancy | 3.2 (2.9) | 3.3 (2.9) | 3.5 (3.1) |
| Completeness (%) | 99.0 (98.5) | 98.3 (96.2) | 97.4 (94.2) |
| $R_{merge}$ (%) | 12.2 (38.1) | 10.8 (34.9) | 9.7 (19.5) |
| Average I/σ (I) | 25.99 (3.64) | 25.56 (3.53) | 33.04 (9.90) |
| Refinement | | | |
| R (%) | 19.4 | 20.7 | 15.1 |
| $R_{free}$ (%) | 23.3 | 24.7 | 19.3 |
| Mean B value (Å$^2$)* | 16.4 | 28.6 | 19.6 |
| B from Wilson plot (Å$^2$) | 12.3 | 24.1 | 19.2 |
| RMS deviation bond lengths (Å) | 0.013 | 0.013 | 0.013 |
| RMS deviation bond angles (°) | 1.889 | 1.592 | 1.638 |
| Number of amino acid residues | 261 | 262 | 261 |
| Number of water molecules | 225 | 102 | 188 |

*Mean B value is for both protein atoms and the solvent molecules.

Example 5-3. Analysis of Thermal Stability of IsPETase Variant Protein

To compare the thermal stabilities of the IsPETase variants, the structures of the IsPETase variants were analyzed and the melting temperatures (Tm) thereof were measured.

Figure 9A:
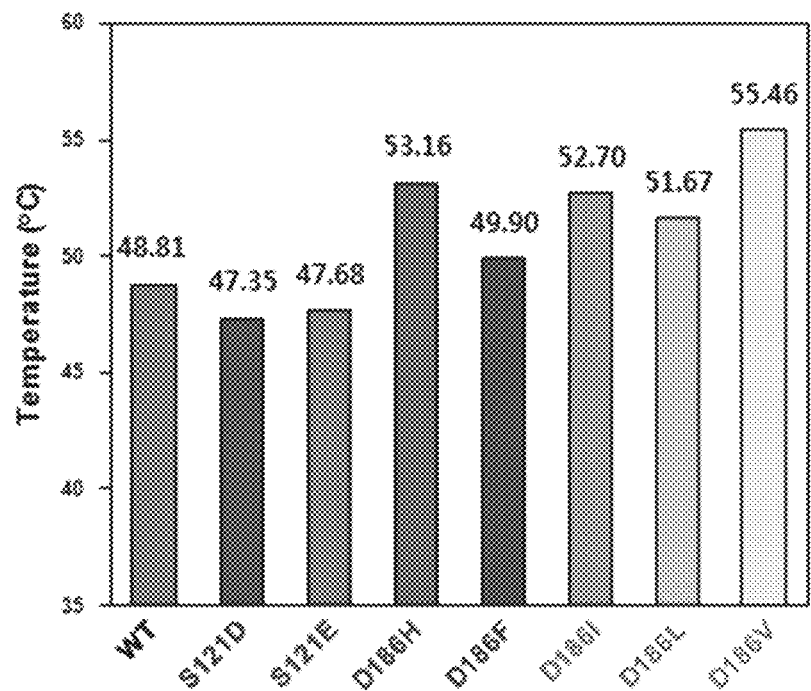
FIG. 9A shows the melting temperature of the IsPETase using a protein thermal shift dye.
Figure 9B:
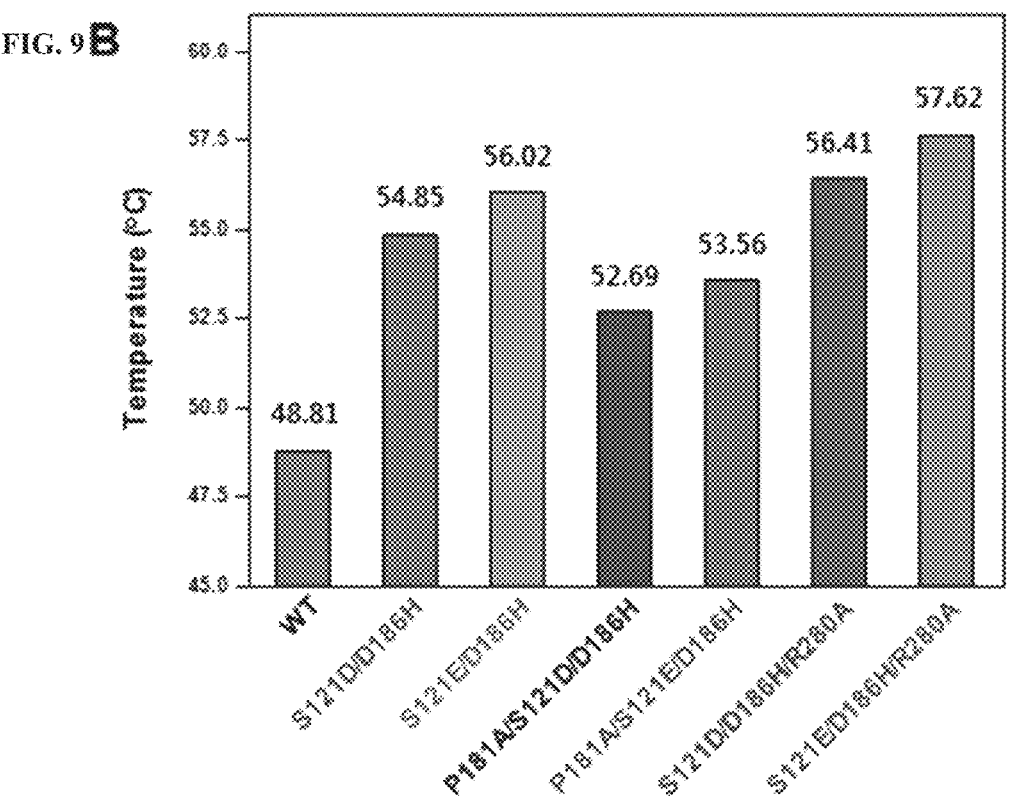
FIG. 9B shows the melting temperature of the IsPETase variant using a protein thermal shift dye.

The melting temperatures were measured based on melting curves with a StepOnePlus Real-Time PCR (Thermo Fisher Scientific) using a protein thermal shift dye (Applied Biosystems). Specifically, 5 ug of the IsPETase was mixed with 20 μl of a protein thermal shift dye, and then, signal changes reflecting protein denaturation were monitored in a temperature increasing region of 25 to 99° C. Based on the melting curves, the melting temperatures of the IsPETase and its variants were determined (FIG. 9A-9B).

The structures and melting temperatures of the IsPETase variants were compared with those of the $\text{IsPETase}^{W/T}$. Referring to FIG. 9A, the melting temperatures of the $\text{IsPETase}^{S121D}$ and $\text{IsPETase}^{S121E}$ were similar to that of the $\text{IsPETase}^{W/T}$.

In one example, Asp186 residues were substituted with hydrophobic residues His, Phe, Ile, Leu, and Val. Thus, the melting temperatures of $\text{IsPETase}^{D186H}$, $\text{IsPETase}^{D186F}$, $\text{IsPETase}^{D186I}$, $\text{IsPETase}^{D186L}$ and $\text{IsPETase}^{D186V}$ were similar to or higher than the melting temperature of the $\text{IsPETase}^{W/T}$. In particular, it was confirmed that the $\text{IsPETase}^{D186H}$ and $\text{IsPETase}^{D186V}$ have the higher melting temperature.

Figure 8C:
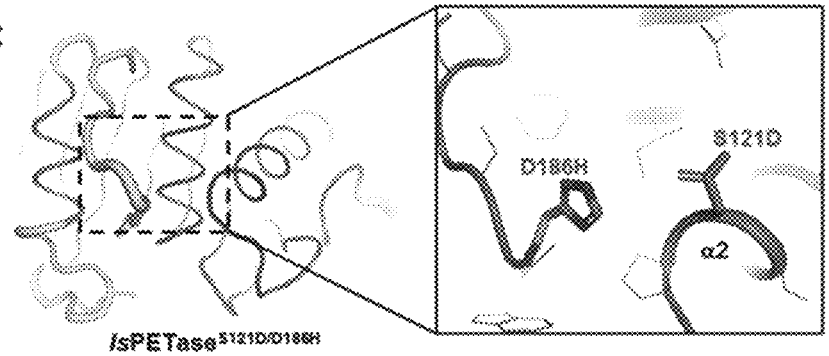
FIG. 8C shows D186H of the β6-β7 connection loop (Asp186-Phe191) of the IsPETase$^{S121D/D186H}$ variant and adjacent α-helix S121D residue thereof.

In the structure of IsPETase$^{S121D/D186H}$, a b-factor value of the β6-β7 connection loop (Asp186-Phe191) was 18.5, and the melting temperature thereof was 54.85° C. Thus, the structure of IsPETase$^{S121D/D186H}$ is more stable than that of the IsPETase$^{W/T}$. However, the IsPETase$^{S121D/D186H}$ did not form a hydrogen bond due to a larger distance (3.9 Å) between Asp121 residue and His186 residue (See FIG. 8C).

Figure 8D:
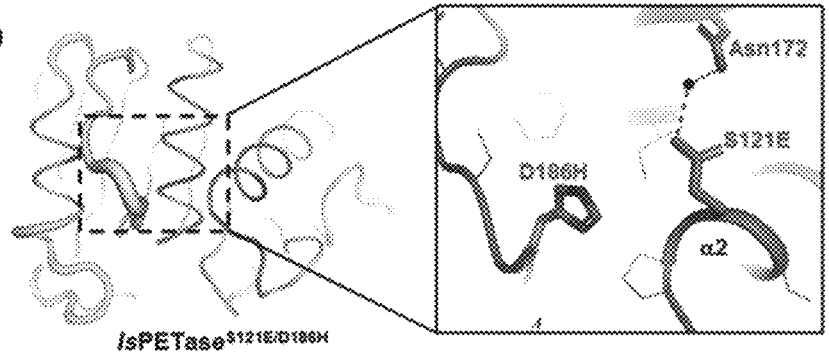
FIG. 8D shows D186H of the β6-β7 connection loop (Asp186-Phe191) of the IsPETase$^{S121E/D186H}$ variant and adjacent α-helix S121E and Asn172 residues thereof. The hydrogen-bonds formed by nitrogen and oxygen are indicated by dotted lines.

Substituting of the Ser121 residue with Glu having a longer amino acid length than Asp was performed. Then, the structure of the resulting IsPETase$^{S121E/D186H}$ was analyzed. The IsPETase$^{S121E/D186H}$ still did not form the hydrogen bonds between the Glu121 and His186 residues. However, the hydrogen bonds were formed between the Glu121 residues and adjacent Asn172 (See FIG. 8D). Referring to FIG. 9B, the melting temperature of IsPETase$^{S121E/D186H}$ was 56.02° C., which was higher than those of the IsPETase$^{W/T}$ and IsPETase$^{S121D/D186H}$. Thus, the IsPETase$^{S121E/D186H}$ could be found to have the higher thermal stability than the IsPETase$^{S121D/D186H}$ via forming the hydrogen bonds in the connection loop.

To determine the thermal stability of the PETase with a normal conformation and stable connection loop in the β-sheet, P181A was further introduced into the IsPETase$^{S121D/D186H}$ and IsPETase$^{S121E/D186H}$, which, in turn, were assayed in terms of the PETase activities. The melting temperatures of the IsPETase$^{P181A/S121D/D186H}$ and IsPETase$^{P181A/S121E/D186H}$ were 52.69° C. and 53.56° C., respectively, and were higher than that of the IsPETase$^{W/T}$ but were lower than those of the IsPETase$^{S121D/D186H}$ and IsPETase$^{S121E/D186H}$, which did not incorporate the P181A. Thus, it could be seen that the Pro181 residue interferes with the increase in the enzyme activity and thermal stability of the IsPETase.

Referring to the fact that the IsPETase$^{R280A}$ was confirmed to have an excellent enzyme activity in the Example 4, we introduced the R280A into the IsPETase$^{S121D/D186H}$, and IsPETase$^{S121E/D186H}$. Then, the PETase activities thereof were measured. The melting temperatures of the IsPETase$^{S121D/D186H/R280A}$, and IsPETase$^{S121E/D186H/R280A}$ were higher than the melting temperatures of the IsPETase$^{S121D/D186H}$ and IsPETase$^{S121E/D186H}$ free of the R280A.

Example 5-4. Activity Analysis of IsPETase Variant Protein

To compare the activities, the decomposition rate of PET by the PETases was analyzed under the same conditions as the Example 4-2.

The PETase activity of the IsPETase variant based on the increasing thermal stability was measured using the PET film as a substrate.

As shown in FIG. 10B, IsPETase$^{S121D}$ and IsPETase$^{S121E}$ have higher enzyme activities than that of the IsPETase$^{W/T}$ at 30° C. However, the IsPETase$^{S121D}$ and IsPETase$^{S121E}$ have similar enzyme activities to that of the IsPETase$^{W/T}$ at 40° C. These variants appear to have lost the enzyme activity at 40° C.

In one example, IsPETase$^{D186H}$, IsPETase$^{D186F}$, IsPETase$^{D861I}$, IsPETase$^{D186L}$, and IsPETase$^{D186V}$ have similar enzyme activities to or lower enzyme activities than that of the IsPETase$^{W/T}$ at 30° C. To the contrary, the IsPETase$^{D186H}$ and IsPETase$^{D186F}$ have higher enzyme activities than that of the IsPETase$^{W/T}$ at 40° C. Especially, the IsPETase$^{D186H}$ maintained the enzyme activity for a long time at the high temperature.

As shown in FIG. 10B, IsPETase$^{S121D/D186H}$ and IsPETase$^{S121E/D186H}$ have higher enzyme activities at 24 hours and 72 hours than that of the IsPETase$^{W/T}$. Further, IsPETase$^{S121D/D186H}$ and IsPETase$^{S121E/D186H}$ have higher enzyme activities than that of the IsPETase$^{W/T}$ at each of 30° C. and 40° C. In particular, the enzyme activity of the IsPETase$^{S121E/D186H}$ was greatly increased compared to IsPETase$^{S121D/D186H}$.

Figure 11:
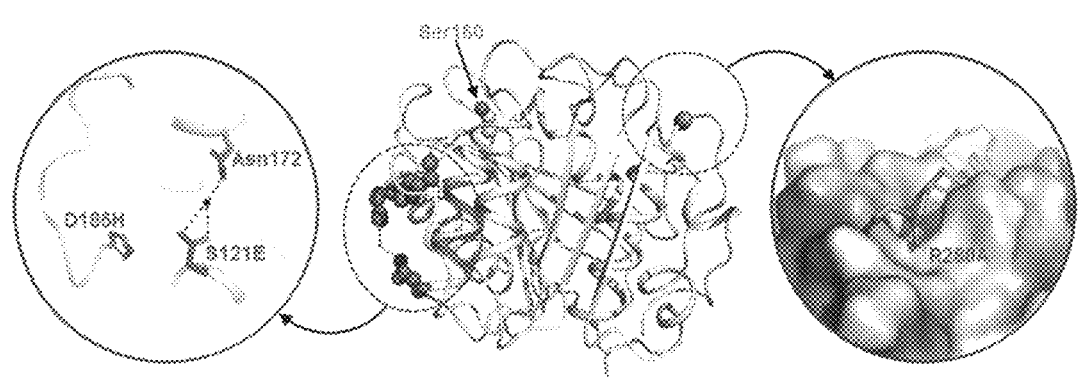
FIG. 11 shows the surface of the crystal structure of the IsPETase$^{S121E/D186H/R280A}$ variant, in which D186H, S121E, and Asn172 residues of the β6-β7 connection loop, and the R280A residue of the sub-site IIc are shown. The hydrogen-bond is indicated by dotted lines.

The IsPETase$^{P181A/S121D/D186H}$ and IsPETase$^{P181A/S121E/D186H}$ were similar to the IsPETase$^{W/T}$ in terms of the enzyme activity due to the P181A residue. The IsPETase$^{S121D/D186H/R280A}$ and IsPETase$^{S121E/D186H/R280A}$ showed higher enzyme activities than those of the IsPETase$^{S121D/D186H}$ and IsPETase$^{S121E/D186H}$. This activity result may correspond to the melting temperature result. In particular, the enzyme activity of the IsPETase$^{S121E/D186H/R280A}$ at 40° C. was at least two times higher than those of the IsPETase$^{S121D/D186H}$ and IsPETase$^{S121E/D186H}$. In the structure of the IsPETase$^{S121E/D186H/R280A}$, Glu121 residue and Asn172 residue form together the water-mediated hydrogen bond as in the IsPETase$^{S121E/D186H}$. Further, the sub-site IIc of the substrate-binding site was extended (FIG. 11).

As a result, the β6-β7 connection loop and the sub-site IIc are located in opposite sides respectively and do not affect each other. Thus, the IsPETase$^{S121E/D186H/R280A}$ exhibited the structural stability due to the β6-β7 connection loop and the extended sub-site IIc. The IsPETase$^{S121E/D186H/R280A}$ may have a synergetic effect of increasing both the thermal stability and enzyme activity.

Example 5-5. Durability Analysis of IsPETase Variant Protein

To compare the persistence of the enzyme activity, PET decomposition rates were analyzed for 10 days under the same conditions as in the Example 4-2.

Figure 12A:
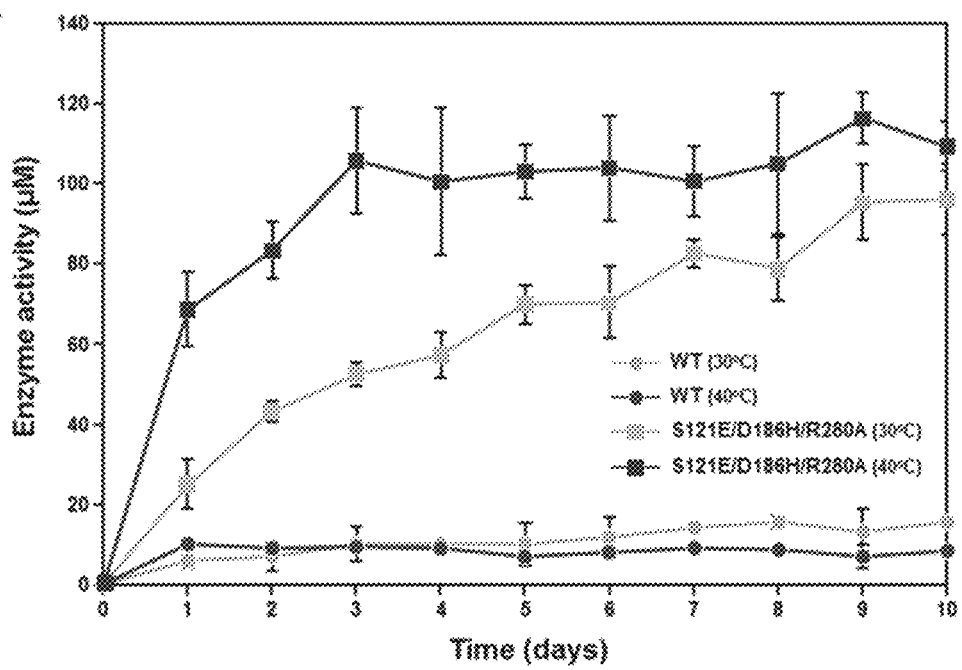
FIG. 12A shows the PETase activity of IsPETase$^{S121E/D186H/R280A}$ variant over time compared with that of IsPETase$^{W/T}$ at 30° and 40° C. The hydrolysis activities of the IsPETase and IsPETase$^{S121E/D186H/R280A}$ variant are measured when using the PET film as a substrate. The PETase activities of IsPETase and IsPETase$^{S121E/D186H/R280A}$ variant are measured at an enzyme concentration of 200 nM. The amount of MHET as produced is monitored by HPLC analysis.

The enzyme activity of the IsPETase$^{S121E/D186H/R280A}$ over time was compared with that of the IsPETase$^{W/T}$. The activity of the IsPETase$^{W/T}$ was maintained by a 10-th day without any significant change. However, the enzyme activity thereof at 40° C. was lower than that at 30° C. On the other hand, the activity of the IsPETase$^{S121E/D186H/R280A}$ rapidly increased on a third day and continued for 10 days. The enzyme activity thereof at 40° C. was higher than that at 30° C. (See FIG. 12A).

In order to compare the thermal stabilities against the high temperature, a further heat inactivation test was performed. The IsPETase$^{W/T}$ and IsPETase$^{S121E/D186H/R280A}$ were heat-inactivated at 50° C. for 1 to 60 minutes. Then, the decomposition rates of the PET by the two PETases under the same conditions as in the Example 4-2 were measured.

Figure 12B:
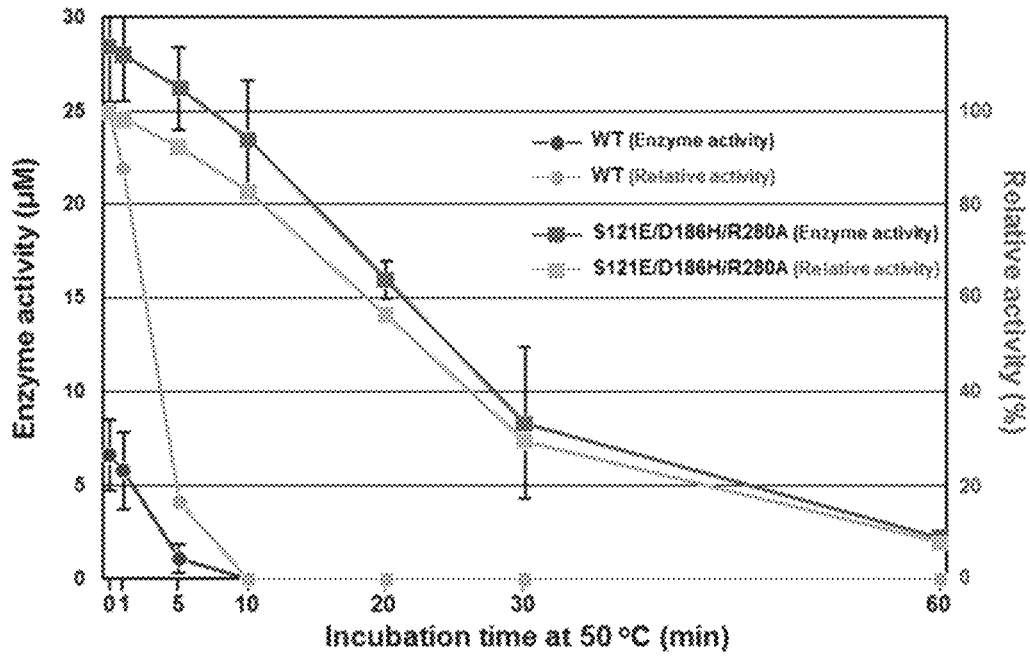
In FIG. 12B, the PETase activity of IsPETase$^{S121E/D186H/R280A}$ variant as heat-inactivated at 50° C. for 1 to 60 minutes is compared with the PETase activity of the IsPETase$^{W/T}$. The hydrolysis activities of the IsPETase and IsPETase$^{S121E/D186H/R280A}$ variant are measured when using the PET film as a substrate. The PETase activities of IsPETase and IsPETase$^{S121E/D186H/R280A}$ variant are measured at an enzyme concentration of 200 nM. The amount of MHET as produced is monitored by HPLC analysis.

The IsPETase$^{W/T}$ had a melting temperature of 48.81° C. When the IsPETase$^{W/T}$ was inactivated for 10 mins at 50° C., the IsPETase$^{W/T}$ did not exhibit the enzyme activity. On the other hand, the IsPETase$^{S121E/D186H/R280A}$ showed a melting temperature of 57.67° C. When the IsPETase$^{S121E/D186H/R280A}$ was inactivated for 20 mins, the enzyme activity thereof was maintained at 50% of the enzyme activity of IsPETase$^{S121E/D186H/R280A}$ which is not subjected to the inactivation. When the IsPETase$^{S121E/D186H/R280A}$ was inactivated for 60 mins, the enzyme activity thereof was maintained at 10% of the enzyme activity of IsPETase$^{S121E/D186H/R280A}$ which is not subjected to the inactivation (See FIG. 12B). As a result, the thermal stability of the PETase against the high temperature was a very important factor for the efficient decomposition of the PET. In this connection, the high thermal stability of the IsPETase$^{S121E/D186H/R280A}$ could increase the PET decomposition rate.

One of ordinary skill in the art to which the present invention belongs may understand that the present invention may be embodied in other specific forms from the foregoing descriptions without departing from the spirit or essential characteristics thereof. In this regard, the Examples as described above are to be understood in all respects as illustrative and not restrictive. The scope of the present invention is to be interpreted as including the meaning and scope of the following claims rather than the detailed descriptions. All changes or modifications derived from the equivalents thereof are included in the scope of the present invention.

I claim:

1. An IsPETase variant consisting of the amino acid sequence represented by SEQ ID NO: 1, wherein the IsPETase variant includes the amino acid substitution at position 280 of SEQ ID NO: 1 with alanine.

2. The IsPETase variant of claim 1, wherein the IsPETase variant further includes any one of the following amino acid substitutions:
   (a) substitution of the amino acid at position 121 of SEQ ID NO: 1 with aspartic acid,
   (b) substitution of the amino acid at position 186 of SEQ ID NO: 1 with histidine, phenylalanine, isoleucine, leucine, or valine, and
   (c) substitution of the amino acid at position 121 of SEQ ID NO: 1 with aspartic acid; and substitution of the amino acid at position 186 of SEQ ID NO: 1 with histidine, phenylalanine, isoleucine, leucine, or valine.

3. The IsPETase variant of claim 1, wherein the IsPETase variant further includes the amino acid substitution at position 121 of SEQ ID NO: 1 with aspartic acid and the amino acid substitution at position 186 of SEQ ID NO: 1 with histidine.

4. The IsPETase variant of claim 1, wherein the IsPETase variant further includes any one of the following amino acid substitutions:
   (a) substitution of the amino acid at position 121 of SEQ ID NO: 1 with glutamic acid,
   (b) substitution of the amino acid at position 186 of SEQ ID NO: 1 with histidine, phenylalanine, isoleucine, leucine, or valine, and
   (c) substitution of the amino acid at position 121 of SEQ ID NO: 1 with glutamic acid; and substitution of the amino acid at position 186 of SEQ ID NO: 1 with histidine, phenylalanine, isoleucine, leucine, or valine.

5. The IsPETase variant of claim 1, wherein the IsPETase variant further includes the amino acid substitution at position 121 of SEQ ID NO: 1 with glutamic acid and the amino acid substitution at position 186 of SEQ ID NO: 1 with histidine.

6. The IsPETase variant of claim 1, wherein the IsPETase variant has a higher PETase activity than a PETase activity of an IsPETase wild-type.

7. A method for decomposing poly(ethylene terephthalate)(PET) comprising treating PET with the IsPETase variant of claim 1.

* * * * *